US012774997B1

(12) United States Patent
Nash et al.

(10) Patent No.: US 12,774,997 B1
(45) Date of Patent: Oct. 27, 2026

(54) MOISTURE DETECTION APPARATUS FOR BUILDINGS

(71) Applicant: UIPCO, LLC, San Antonio, TX (US)

(72) Inventors: Justin Royell Nash, Little Elm, TX (US); Soon Fatt Hoo, Tahlequah, OK (US); Ashley Raine Philbrick, San Antonio, TX (US); Matthew Robert Byrd, Boerne, TX (US); Yevgeniy Viatcheslavovich Khmelev, San Antonio, TX (US)

(73) Assignee: United Services Automobile Association (USAA), San Antonio, TX (US)

( * ) Notice: Subject to any disclaimer, the term of this patent is extended or adjusted under 35 U.S.C. 154(b) by 1218 days.

(21) Appl. No.: 17/661,091

(22) Filed: Apr. 28, 2022

(51) Int. Cl.

| | |
|---|---|
| ***G01N 33/00*** | (2006.01) |
| ***G01M 3/38*** | (2006.01) |
| ***G01M 3/40*** | (2006.01) |
| ***G01N 21/3554*** | (2014.01) |
| ***G01N 21/359*** | (2014.01) |
| ***G01N 22/04*** | (2006.01) |
| ***G01N 23/083*** | (2018.01) |
| ***G01N 27/12*** | (2006.01) |
| ***G08B 21/20*** | (2006.01) |

(52) U.S. Cl.
CPC ......... *G01N 33/00* (2013.01); *G01N 21/3554* (2013.01); *G01N 21/359* (2013.01); *G01N 22/04* (2013.01); *G01N 23/083* (2013.01); *G01N 27/121* (2013.01); *G08B 21/20* (2013.01); *G01M 3/38* (2013.01); *G01M 3/40* (2013.01)

(58) Field of Classification Search
CPC .. G01N 33/00; G01N 21/3554; G01N 21/359; G01N 22/04; G01N 23/083; G01N 27/121; G08B 21/20; G01M 3/38; G01M 3/40
USPC ............................................................ 73/643
See application file for complete search history.

(56) References Cited

U.S. PATENT DOCUMENTS

| | | | | |
|---|---|---|---|---|
| 7,243,050 | B2 * | 7/2007 | Armstrong | G08B 21/20 702/182 |
| 9,618,940 | B1 * | 4/2017 | Michini | G08G 5/55 |
| 10,671,767 | B2 * | 6/2020 | Duff | G06Q 10/06 |
| 11,549,837 | B2 * | 1/2023 | Klicpera | G01M 3/26 |
| 2015/0192466 | A1 * | 7/2015 | Kusukame | G01N 21/35 250/339.04 |

* cited by examiner

*Primary Examiner* — Marrit Eyassu
(74) *Attorney, Agent, or Firm* — Plumsea Law Group, LLC

(57) ABSTRACT

A method, system, and device assembly of inspecting structural conditions in hard-to-reach areas in a building are disclosed. The embodiments are configured to allow for the deployment of a device through an opening for a standard outlet in a wall, whereby the device will transmit data regarding its location and external conditions to a nearby monitoring (controller) device. Upon arriving at a section in which damage is observed, the device can automatically transmit a signal indicating its current location.

20 Claims, 12 Drawing Sheets

MOISTURE DETECTION APPARATUS FOR BUILDINGS

TECHNICAL FIELD

The present disclosure generally relates to inspections and monitoring of moisture, and specifically to a method and system of sensing and measuring the presence of moisture in and behind walls.

BACKGROUND

Most buildings, including commercial and residential buildings, are typically exposed to the elements during the course of their life. Various forms of precipitation such as rain, sleet, snow, hail, and humidity all contribute to the deterioration of buildings over time, as well as environmental conditions such as wind, heat and cold, solar rays, shifting earth, pests, etc. A building component such as an interior wall (e.g., drywall, plywood, panels, plaster, sheetrock, etc.) that serves an integral structure of a residential home must remain protected against certain environmental elements such as rain water or heat/cold, as well as damage from plumbing damage (e.g., leaks and flooding). However, over the course of the component's installed life, exposure to such elements that can cause the component to deteriorate and begin to fail is sometimes unavoidable.

A water-damaged wall can represent a substantial loss to residents, and a substantial inconvenience to home owners and other users. In many cases, one of the most challenging first steps is to determine whether moisture damage has occurred, as the signs are not always immediately obvious. The resident must then locate the exact area in which moisture has spread so that an appropriate method for repairing or removing the moisture can be determined. Consumers often engage in a trial-and-error approach until the water leak or other moisture damage is located and eliminated, and resources and time are expended in simply identifying the location of its presence with some level of accuracy. Furthermore, access to the interior of a wall in order to search for the water damage typically requires the wall to be broken. A detection system and method that are capable of remotely and unobtrusively determining the location and extent of moisture damage in a practical and cost-effective manner would therefore be beneficial.

There is a need in the art for a system and method that addresses the shortcomings discussed above.

SUMMARY

In one aspect, a structural inspection assembly is described. The assembly includes a first device including a first magnetic component, and a first sensor configured to assess moisture content, as well as a second device including a second magnetic component with a magnetic field strong enough to exert a magnetic pulling force on and maintain a grip of the first magnetic component through at least a ½ inch thickness of drywall.

In another aspect, a method of detecting damage to a structure is disclosed. The method includes a first step of receiving, by an onboard computing system of a structural inspection device located at a first position, a first navigation command, and a second step of causing a propelling mechanism of the structural inspection device to move the structural inspection device from the first position to a different, second position in response to the first navigation command. A third step includes measuring, while at the second position and via a first sensor of the structural inspection device, a first moisture content level for a structural component within range of the first sensor, and a fourth step of determining, at the onboard computing system, the first moisture content level exceeds a preselected threshold. The method also includes a fifth step of generating, via the onboard computing system, a first notification including information about the first moisture content level and a description of the location of the second position, and a sixth step of transmitting over a network and via a communications module of the structural inspection device, the first notification to a client computing device.

In another aspect, a system for detecting damage to a structure includes a processor and machine-readable media including instructions which, when executed by the processor, cause the processor to receive, by an onboard computing system of a structural inspection device located at a first position, a first navigation command, and to cause a propelling mechanism of the structural inspection device to move the structural inspection device from the first position to a different, second position in response to the first navigation command. In addition, the instructions cause the processor to measure, while at the second position and via a first sensor of the structural inspection device, a first moisture content level for a structural component within range of the first sensor, and to determine, at the onboard computing system, the first moisture content level exceeds a preselected threshold. Furthermore, the instructions cause the processor to generate, via the onboard computing system, a first notification including information about the first moisture content level and a description of the location of the second position, and transmit over a network and via a communications module of the structural inspection device, the first notification to a client computing device.

Other systems, methods, features, and advantages of the disclosure will be, or will become, apparent to one of ordinary skill in the art upon examination of the following figures and detailed description. It is intended that all such additional systems, methods, features, and advantages be included within this description and this summary, be within the scope of the disclosure, and be protected by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like reference numerals designate corresponding parts throughout the different views.

DETAILED DESCRIPTION

Figure 1:
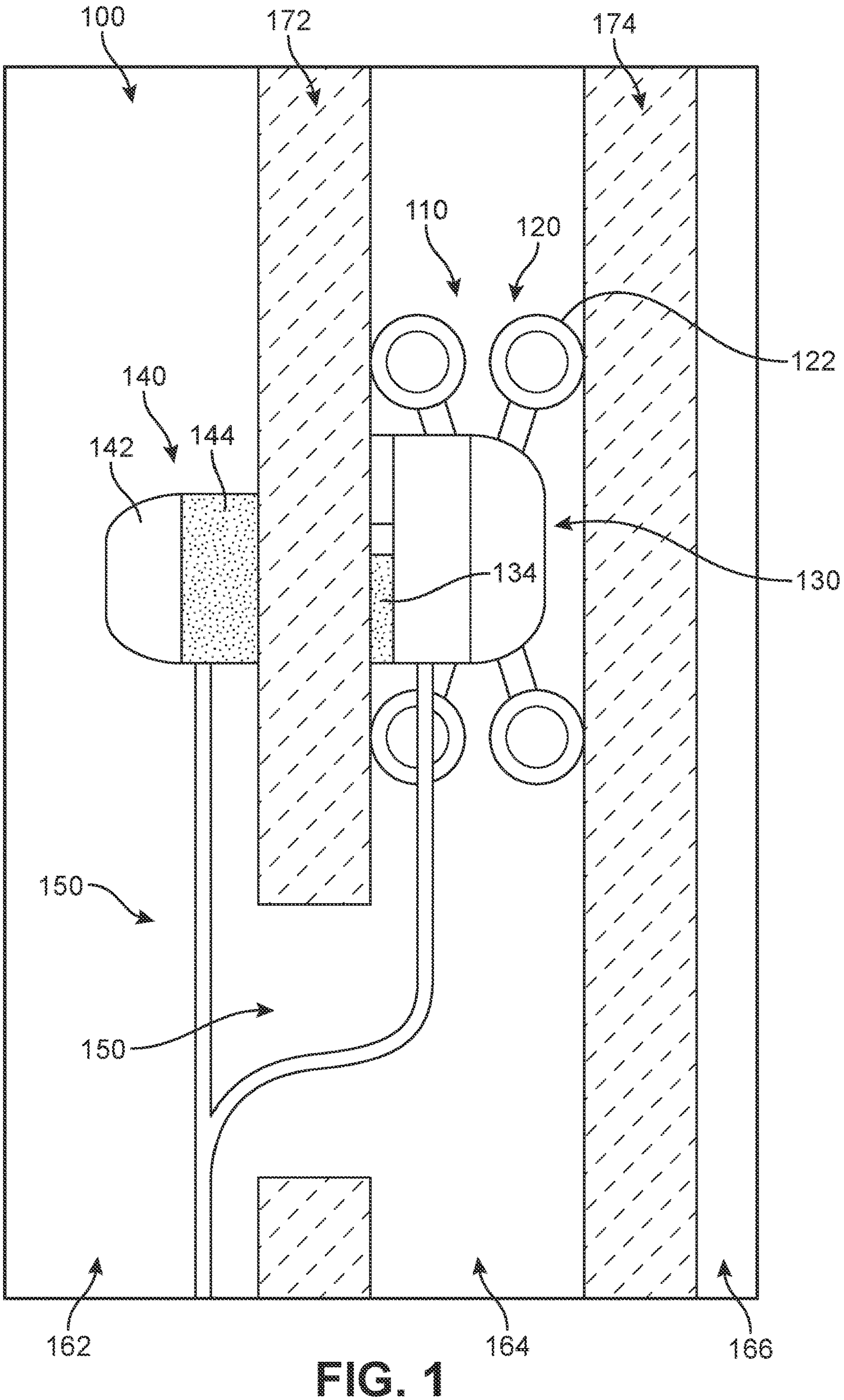
FIG. 1 is a side view of a structural inspection assembly including a structural inspection device and controller, according to an embodiment.

The embodiments provide a method and system to improve the detection of moisture in and behind building materials. The proposed embodiments enable the highly accurate detection of moisture in materials in a building (e.g., roof or wall materials such as plywood, shingles, sheet rock, siding, etc.). In one example, the system includes a device that is disposed inside a wall, between opposing sheets of drywall. The device can move within an interior space of the wall and can detect multiple issues and problems. The device includes features allowing it to navigate up and down within the interior space between the two adjacent pieces of drywall. For example, the device can include provisions that allow it to move as a wall crawler (i.e., move along vertical surfaces) along the interior faces of the two walls. In one embodiment, an external user-guided controller is used to move the in-wall device.

Early detection of water leaks can substantially lessen the severity of water damage. As noted above, water can cause damage to structures, which can cause costly repairs and/or make the structure uninhabitable due to mold, for example. In an example, a structure can include a home, building associated with a business, and/or other type inhabitable structure. When structures are in flood plains, an owner of the structure may be likely to purchase flood insurance because a known risk for a flood exists. However, a structure may still suffer water damage, even when the structure is not in a flood plain. For example, rain may cause an accumulation of standing water, which can cause damage to a property, but may not be present in a large enough quantity to be classified as a flood. Alternatively, and/or in addition, the accumulation of standing water can be caused as a result of landscaping that does not provide proper drainage of water. For instance, landscaping can be performed around a structure, which can cause water to drain toward the structure and accumulate next to the structure, rather than drain away from the structure. As such, a depth of the water may increase to a point where the water can enter the structure and cause damage.

Alternatively, and/or in addition, water damage can be caused to a structure as a result of wind driven rain. In an example, wind can cause rain to travel near horizontally and/or upward. For example, if wind causes rain to travel near horizontally, the rain can be driven vertically upon meeting an object or structure. In an example, when horizontally driven rain meets an exterior wall of a structure, the rain can be driven vertically. The rain can be driven vertically under an eave of the structure and can contact a soffit of the structure and/or vents placed within the soffit. As a result, the rain can enter the soffit vent and can cause damage to the structure. In another example, water damage caused by improper landscaping and/or wind driven rain may not be covered under an insurance policy associated with the structure.

Furthermore, leaks often occur in pipes that are hidden behind walls or in cracks in foundations or other fluid pathways that are not readily observable. When the leaks are eventually observed, significant damage may have already occurred. It is therefore desirable to place moisture detection devices in locations where leaks or ingress of water may occur to provide warning to designated people of a detection event so they can take corrective action immediately (such as shutting a water supply valve), and/or repair any structural damage.

As one example, roofing shingles are designed to help keep rain water from getting into a structure. However, a storm event may compromise the integrity of the roofing system, leading to recurring water leaks in the attic or upper level(s) of the building without the occupant's knowledge. In many cases, these leaks may not be immediately evident, as some homeowners may not frequent their attics, or may not otherwise regularly inspect their home's systems. As such, these system integrity failures may go undetected for weeks, months, or years until evidence presents itself more apparently to the homeowner. This delay in promptly detecting such building system failures may lead to additional damage to the building. For example, one eventual visual indicator for an undetected roof leak may be a resulting dark spot or stain of dampness and/or mold growth on the ceiling of an interior roof where the leak dripped over the course of many rains. This additional damage created by the undetected interior damage may cause building owners to have to spend significantly more to repair the building, as they pay to fix not only the underlying system failure (e.g., the leaky roof) but also the damage caused by not promptly detecting the failure (e.g., the mold growth in an attic and the staining on the interior ceiling).

Furthermore, as a general matter, negative effects of moisture on building envelopes are well known. Some effects can include (a) loss of material in the affected structure due to changes in water volume when changing the physical phase and/or when chemical substances contained in water (e.g., salt) react with the affected material (e.g., plaster), (b) worsening of user's health and comfort due to the growth of mold in non-nutritive moist materials with traces of organic matter contamination, and (c) increase in energy consumption due to the lower thermal resistance of moist materials compared to dry materials leading to a lower degree of insulation of a building. These and other negative effects can result in outcomes that cause (a) catastrophic consequences for the integrity of the building, (b) illness and discomfort to users, and (c) high levels of energy waste, resulting in both increased economic costs and pollution. Thus, early detection of moisture in a building offers significant benefits to the building owner.

As will be described in greater detail below, in different embodiments, the systems can include a moisture detection assembly that may be utilized to monitor the presence of water (e.g., leaks, floods, etc.) in a particular location, such as a home (e.g., under the sink, in the walls, in the attic, near toilets, near washing machines, near dishwashers, near water heaters, among other locations), a commercial building, and/or other suitable locations. The moisture detection device may include various components (e.g., a communication module, a computing device, a controller, a battery, and/or an array of sensors) installed in a housing that includes a wall crawling mechanism to facilitate the navigation of the device along vertical surfaces. In one example, the device sensors can include infrared, moisture, thermal, or other imaging cameras. In some embodiments, the device housing includes a magnet that can be manipulated from outside the wall (i.e., by a person) to scour different interior areas. In other embodiments, the device can move autonomously and can include a docking station to recharge. In some embodiments, the device includes a structural assessment machine learning (ML) model that can determine if mold, pests, or other unwanted objects are found within a wall. In another example, the device also includes the physical structures and control software to autonomously move vertically within a wall.

For purposes of clarity, an overview of one embodiment of the proposed systems and methods is illustrated with reference to FIG. 1. In FIG. 1, an embodiment of a first moisture detection assembly ("assembly") 100 is schematically depicted. The assembly 100 includes a monitoring device 110 and a controller device 140. In this case, the monitoring device 110 and controller device 140 are in communication with and/or supplied power via a wired connection 150. However, in other embodiments, the assembly 100 is wireless.

As shown in FIG. 1, between a first drywall 172 and an opposing second drywall 174 is a first interior space 164. A user (not shown in FIG. 1) who is positioned outside of the first interior space 164—for example, in a first room 162 partially defined by the exterior facing side of first drywall 172, or in a second room 166 partially defined by the exterior facing side of the second drywall 174—can push or otherwise deploy the monitoring device 110 into the first interior space 164. For example, the monitoring device 110 can be inserted through an aperture 152 in the first drywall 172 (such as a wall outlet or other pre-formed opening).

In different embodiments, the monitoring device 110 includes a plurality of components disposed in a housing 130 that are configured to permit the monitoring device 110 to communicate with other devices and/or to detect or monitor various external conditions. In this embodiment, the plurality of components can be understood to include at least a wireless communication module (such as near-field communication (NFC), Radio Frequency Identification (RFID), or Bluetooth® technology) or other type of short-range wireless communication sensor, such as a sensor employing Wi-Fi or similar wireless technology, and a battery or other power source that is configured to supply electrical power to the sensor device. In some embodiments, the plurality of components further includes additional sensors that are configured to measure parameters associated with movement of the monitoring device 110. For example, in some embodiments, the plurality of components can include an accelerometer and/or gyroscope configured to measure acceleration and rotational values and a force sensor configured to measure force values. In some embodiments, the accelerometer and/or force sensor may be used to measure parameters, such as acceleration, speed, orientation, force, etc., associated with the pattern of movement of the monitoring device 110. In addition, in other embodiments, the monitoring device 110 may also include components configured to detect or capture information associated with characteristics and conditions of the external environment such as temperature, pressure, moisture, light, chemical composition, obstructions, and other external conditions.

The embodiment of FIG. 1 further includes controller device 140. In this case, the controller device 140 includes a magnetic base 144 that provides a strong attractive force on a magnetic component 134 included in housing 130 of the monitoring device 110. Magnetic materials that can be used can include neodymium magnets, or other permanent magnets that are capable of exerting a magnetic pulling force through at least 4 to 1% (or more) thickness of wood, plastic, aluminum, concrete, water, Teflon, copper, and other wall materials or structural components. In some embodiments, the controller device 140 can be manually manipulated by the user to move the in-wall monitoring device 110. In other words, as the controller device 140 is moved along the exterior surface of the first drywall 172, there is a corresponding motion of the magnetically linked monitoring device 110 along the interior surface of the same drywall. Furthermore, in another embodiment, the monitoring device 110 can include a stabilization mechanism such as a spring-biased 'scissor' hinge that deploys wheels 122 on the interior surfaces of the opposing sheets or surfaces of drywall. In this example, there are two spring-loaded hinges 120 with accompanying wheels that exert pressure on either side and allow the monitoring device 110 to maintain its position as it is moved.

Figure 2:
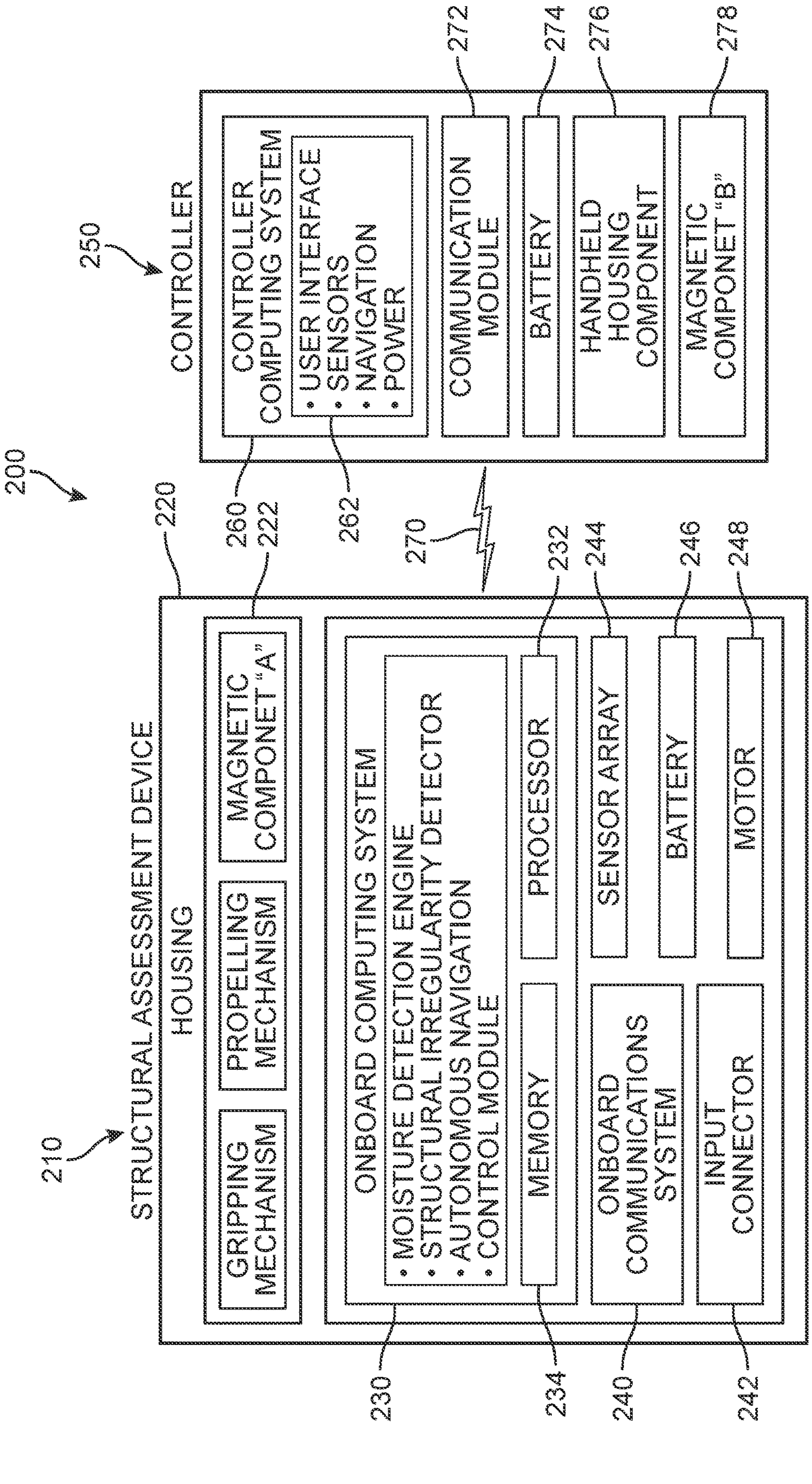
FIG. 2 is a schematic diagram of a structural assessment assembly system, according to an embodiment.

In order to provide the reader with a greater appreciation of the embodiments to the reader, FIG. 2 depicts a schematic diagram representing the architecture of one embodiment of a moisture monitoring assembly ("assembly") 200. As shown in FIG. 2, the assembly 200 includes a structural inspection device ("inspection device") 210 and a controller device ("controller") 250. In different embodiments, either or both of the structural inspection device 210 and controller 250 can be configured to communicate over one or more networks 270 to a remote server ("server"), as well as with each other. As will be discussed below, controller 250 can refer to a passive controller that can be used to cause mirrored movements by the structural inspection device (e.g., as shown in FIG. 1), an electronic controller such as a joystick or other wired or wireless remote control, or a software-based user interface running on a computing device such as a desktop or laptop computer or mobile phone, tablet, or other computing device that transmits to and receives signals from the structural inspection device 210.

As a general matter, networks 270 could include one or more Wide Area Networks (WANs), Wi-Fi networks, Bluetooth or other Personal Area Networks, RFID, cellular networks, as well as other kinds of networks. It may be appreciated that different devices could communicate using different networks and/or communication protocols. The communication module may include a wireless connection using Bluetooth® radio technology, communication protocols described in IEEE 802.11 (including any IEEE 802.11 revisions), Cellular technology (such as GSM, CDMA, UMTS, EV-DO, WiMAX, or LTE), or Zigbee® technology, among other possibilities. In many cases, the communication module is a wireless connection; however, wired connections may also be used. For example, the communication module for either device may include a wired serial bus such as a universal serial bus or a parallel bus, among other connections.

Thus, in different embodiments, the structural inspection device 210 may include provisions for communicating with, and processing information from, nearby networks and/or devices, represented as an onboard communications system 240. Onboard communication system 240 may include radios or other provisions for communicating using one or more communication methods. In particular, onboard communication system 240 includes provisions for communicating with other nearby devices and data services over networks 270. For example, a communication component could include a Wi-Fi radio, a Bluetooth radio, and/or a cellular network radio. In different embodiments, onboard communications system 240 may further be provided and utilized to communicate recorded information from the inspection site to an external location, such as computer server, which may be associated with an insurance carrier such as USAA®. Onboard communications system 240 may be, or may comprise, a network communication card such as an Ethernet card, a WiFi card, or any other communication mechanism. However, onboard communications system 240 could take any form and is not limited to these examples. Onboard communications system 240 might encrypt data that it communicates, in order to protect the security and/or privacy of the data.

In some embodiments, onboard communications system 240 may communicate data recorded by device (e.g., data stored in memory) to an external location, such as remote server. For example, server may be operated by an insurance company, and may collect data in order to learn about maintenance/repair needs and other analytics relative to structure where the structural inspection device is located. onboard communications system 240 may initiate communication sessions with server or, as another example, server may contact structural inspection device, through onboard communications system 240, in order to receive data that has been stored by the structural inspection device. Additionally, data from sensors, onboard clock and/or memory may be communicated directly to server, over a network.

In some embodiments, onboard communication system 240 can be configured to provide communication with a ground or central communication system. These communication components, such as an antenna, enable information to be transmitted between the systems via a network or signal processing. Thus, the type of communication components used in each communication system can be selected according to the type of communication channel used. In some cases, a cellular network could be used so that each communication system includes a cellular radio or other component that enables cellular communication. Using a cellular network may enable information to be exchanged while structural inspection device 210 is traveling in areas where Wi-Fi or other local networks might be unavailable. In other cases, networks could comprise any kind of local area network and/or wide area network. In some cases, network may be a Wi-Fi network.

In some embodiments, in order to better accommodate the transmission of signal in a water or other fluid-based environment, the onboard communication system 240 can be configured to emit data encoded or carried by sound waves. In other words, in some cases, due to water causing an attenuation of electromagnetic waves, an alternative communication protocol may be used by the system. For example, sound waves from controller 250 may be generated that represent specific data such as information or commands or other requests, and the onboard communication system 240 can receive or ‘pick up’ these sounds (e.g., pulses). In response, the onboard communication system 240 can encode responses or other information in sound that will be received by a communication module 272 of the controller 250. As a general matter, the medium of water is understood to carry sound waves well, and the speed of sound in water provides an additional advantage in offering accurate “ranging” from the structural inspection device 210 to the receiver (i.e., the controller 250) using, for example, a time-of-broadcast packet.

For example, in some embodiments, a receiver can be configured to provide or function as a Wi-Fi bridge, and/or as the original transmitter. In such cases, rather than transmitting data over an antenna via a wireless protocol, the receiver will include or make use of a speaker that also encodes data. The receiver can then pick up those encoded sound waves and transmit the information to a cloud backend via Wi-Fi. For example, a sound sensor included in the device can be coupled to the onboard communication system 240. As one non-limiting example, the sound sensor can include a piezoelectric transducer, such as those used as electrically powered output devices that generate audio. Based on the location of the receiver, the typical minimum sound level requirement for such detector/devices, and the form of the signal, the sound energy impinging on the sound sensor can be of sufficient energy to be received and translated, in some cases without needing any other electrical power.

In addition, in different embodiments, structural inspection device 210 may include an onboard computing system 230 comprising one or more processors 232 and memory 234. Memory 234 may comprise a non-transitory computer readable medium. Instructions stored within memory 234 may be executed by the one or more processors 232. Memory 234 may further be provided and utilized to store data readings and/or timestamps in device. For example, memory may comprise, or may otherwise make use of, magnetic or optical disks, volatile random-access memory, non-volatile random-access memory, or any other type of storage device. There may be sufficient data storage capacity to store several hours or several days (or months) worth of readings.

In addition, onboard computing system 230 can include an optional navigation system configured to enable autonomous or semi-autonomous navigation. In other words, in some embodiments, the structural inspection device 210 can be configured to conduct an inspection of a portion of the building with little to no guidance, essentially eliminating the need for a controller device. However, in other embodiments, the assembly 200 is semi-autonomous, such that control is maintained by the user but an auto-inspection mode may also be enabled that causes the structural inspection device 210 to automatically travel a path (e.g., back and forth in undulating lines) along the interior space between the drywalls or other structural components. The navigation system may comprise any system capable of providing directions and/or other kinds of routing information between two or more positions as well as determining the device’s current location. In some embodiments, a GPS receiver that can receive/send GPS information may be included. In other cases, the navigation system can include other receivers capable of receiving global or local positioning information. In some cases, navigation system may provide directions in outdoor and/or indoor environments.

In different embodiments, navigation module will work in conjunction with the computer vision module, configured to interpret characteristics of the real 3D world into metric data through the processing of 2D image planes. It should be understood that the system’s computer vision module will incorporate processing techniques that allow the device to perform tasks such as machine inspection, navigation, 3D modeling, building and surveillance, as well as interaction with the environment. The accomplishment of these applications requires the execution of several algorithms that reside on onboard computing system 230, which process 2D images and provide 3D information. Some of these algorithms perform object recognition, object tracking, pose estimation, ego-motion estimation, optical flow and scene reconstruction. The navigation module will monitor the motion of the structural inspection device from one place to another during processing of sensor data. In one embodiment, the structural inspection device 210 is configured to extract essential information for its state (kinematics and dynamics—state estimation), build a model of its surroundings (mapping and obstacle detection) and even track sequential objects of interest (target tracking) to enhance the perception capabilities. Thus, by combining localization and perception capabilities, the robotic platform is enabled for guidance tasks. The platform processes information from perception and localization parts to decide its next move according to the specified task (e.g., detecting and locating moisture-rich zones). In one embodiment, the realization of actions derived from navigation and guidance tasks is performed by a controller module of the onboard computing system 230 which manipulates the inputs to provide the desired output enabling actuators for force and torque production to control the vehicle's motion. In some embodiments, different controllers can be used to fulfill mission enabled requirements (position, velocity and acceleration control).

Furthermore, in different embodiments, onboard computing system 230 may include or be in communication with sensor array 244 (also referred to simply as "sensors" 244) for measuring orientation, altitude, and/or acceleration. For example, sensors can include a gyroscope, an altimeter, and an accelerometer. In different embodiments, sensors 244 may also include a camera for capturing images and other light-based data for receipt by the image processing system. Camera may comprise any kind of camera, including any kind of digital camera, as well as a camera configured to capture infrared, x-ray, ultraviolet, and visible light signals. Other examples of sensor devices include, but are not limited to, cameras, infrared sensing devices, moisture sensing device, sound sensing (to listen for rodents, running water, material density, insulation gaps, etc.), gas sensing devices, material sensing devices, x-ray, thermal sensing devices, and the like.

In different embodiments, onboard computing system 230 includes a moisture detection engine, structural irregularity detector/data analysis engine, autonomous navigation module (route determination engine), and a sensor management engine. Each of these engines are logical entities that may be implemented in the form of software (e.g., computer-executable instructions) stored in a memory of, and executing on a processor of the structural inspection device 210, server, or another computer system. As a general matter, the data analysis engine may analyze data retrieved by sensors 244. Analysis by data analysis engine may include comparing image data to stored coordinates to identify additional or replacement images that may need to be gathered. Route determination engine may be utilized to manage the structural inspection device 210, which may include confirming that the structural inspection device 210 remains on a planned path based on a particular target, task, or goal. Route determination engine (also referred to herein as an autonomous navigation engine) may also determine modifications to a route based on gathered data. For example, if additional images are needed of a certain location, which may include a different perspective or angle, route determination engine may request the structural inspection device 210 to vary the planned path accordingly, which may change the parameters of the mission. In addition, the sensor management engine controls sensors 244. This control may include determining which sensor of a plurality of sensors are gathering data, the operating characteristics of said data gathering (e.g., the level of zoom of a visible light camera), where a sensor is aimed or directed, or any other sensor performance control variables as would be recognized by those skilled in the art.

In some embodiments, the onboard computing system 230 further includes an image capture and processing system, also referred to simply as image processing system. Image processing system may be used to store, process, and transmit image information. Additionally, in some cases, image processing system can receive navigation other coordinate/navigation information about one or more target locations. To facilitate these tasks, image capture and processing system may include one or more processors as well as memory. Memory can store instructions for programs that facilitate storing, processing, and transmitting image information. The processed image data can be provided to navigation module to execute a path around a building as the structural inspection device 210 approaches its final destination.

In different embodiments, sensors 244, in conjunction with moisture detection engine and structural irregularity detector for onboard computing system 230, can also be configured to perform and apply Non-Destructive Testing (NDT) techniques. According to the ISO standard definitions, a technique is classified as NDT if it is an analysis technique used to evaluate the properties of a material, component, or system without causing damage. Then, an NDT technique is a specific way of using an NDT method, and an NDT method is a discipline that applies a physical principle in NDT. Sensors 244 of the embodiments described herein are configured to detect, monitor, and/or measure, among others, acoustic emission, electromagnetic testing, gamma- and X-radiology, leak testing, liquid penetrant testing, magnetic particle testing, neutron radiology and gauging, ultrasonic testing, etc. In this way, the intrusive nature of the destructive techniques and the alterations they cause in the integrity of the structure are avoided with NDT techniques, in addition to gaining in objectivity and speed in results generation.

For purposes of this application, the structural inspection device 210 can be understood to carry one or more sensors 244 that are configured to apply NDT techniques for the detection and characterization of moisture severity in buildings, both superficial and internal, as well as determine, using ML models, whether there are any structural characteristic present that warrant further investigation. As some non-limiting examples, structural inspection device 210 can includes (1) sensors that employ electrical tomography in the spatial analysis of moisture in porous building materials (such as bricks and cement) of various thicknesses, (2) sensors that use gamma-rays and X-rays to determine moisture diffusivity, (3) sensors including dielectric and microwave meters to analyze moisture content, (4) sensors that use laser scanning, involving a procedure to automatically show where moisture appears in a building and assess moisture saturation and movement in building materials, respectively, (5) sensors that apply InfraRed Thermography (IRT) and electrical resistance measurement for in situ assessment of superficial moisture, (6) sensors that use Ground-Penetrating Radar (GPR) for internal moisture detection, (7) sensors using the near-infrared (NIR) spectrum via a non-contact, light-reflection type of moisture sensor that is based on a water molecule's light-absorbing characteristics the near-infrared (NIR) spectrum, and/or other sensors that can collect data relevant to the detection of moisture. Thus, the moisture detection engine can employ a wide range of sensors to accurately identify moisture content levels and the spread of the moisture across different materials and surfaces. In some embodiments, the moisture detection engine can also include a model that can predict the path of moisture in order to recommend a preemptive treatment of areas that are likely to be impacted if the moisture ingress is not addressed.

In one example, the sensors include a 2-D camera and/or a 3-D camera. Alternatively, and/or in addition, the camera can possess functionality for recording an infrared spectrum and/or electromagnetic spectrum. In an example, an image captured by the camera that includes the infrared spectrum can be used to find points where heat is escaping the structure. In an example, if heat escapes from the structure at particular points, this may be an indication that water can enter through those same points. For instance, if heat escapes from a crack in a wall, water may enter through the crack. As such, a determination for points associated with a potential for water entry can be determined based on an image captured by the camera that includes the infrared spectrum.

In different embodiments, sensors 244 may capture (e.g., produce, generate, and/or acquire) a number of multispectral images (e.g., a number of digital images) of a wall or roof or other structural feature. For example, a sensor may capture a number of images of a roof that has been damaged due to, for instance, a storm, wind, hail, falling tree(s), water, and/or fire, among other causes of damage. The sensor can capture images of a portion(s) of the roof (e.g., the damaged portion(s)) and/or images of the entire roof. As an example, after the sensor captures an image of a roof, the structural inspection device (e.g., its position or pose) can be adjusted (e.g., moved), and the sensor can then capture a different image of the roof (e.g., an image of a different portion of the roof).

As another example, structural inspection device 210 may include mechanical devices that may be actuated to allow it to physically contact a structure as part of the inspection process. For instance, mechanically actuated devices may poke, hammer, tap, or create friction against a structure in order to collect data. In one example, such devices may work in conjunction with other devices to collect such data. For instance, a mechanical device may tap a structure and a sound sensor may listen to the sound produced by the mechanical device tapping the structure and diagnose a condition of the structure.

In some embodiments, the onboard computing device can be configured to conduct an analysis to determine recommendations to make certain immediately needed repairs to the structure of a dwelling or structure. For instance, a hole may have been detected in the roof (via one or more sensors 244), requiring immediate repair. As another example, one or more infrared sensors may have detected a water leak, energy leak, or energy host spot. An environmental sensor may have detected a water leak or any contaminant, such as mold, which adverse to human health. Piezoelectric sensors may be included to detect debris. As another example, dwelling roof temperature analysis may have detected excessive cold temperatures within the attic of the dwelling which could be indicative of a roof leak or insulation degradation. Based upon certain analysis, the assembly may recommend preventive maintenance to the structure.

In some embodiments, the confidence level may be based on one or more of the following: number of images taken, a resolution of each image, resolution average of a percentage of images, or an image taken of the wall (or other structural component) at a particular perspective. One or more of the aforementioned may help in meeting a minimum threshold confidence level of accuracy in subsequent analysis by the moisture detection engine and/or data analysis engine. In some embodiments, an assessment may be sent to the owner via an electronic message. The electronic message may be a short message service (SMS) text message, an electronic mail (e-mail) message, multimedia message service (MMS) message, or other forms of electronic communication. An electronic message may include an image of the damage to the wall or a graphical depiction of the moisture content levels, among other things. In other examples, the user may be able to connect the structural inspection device to their own computer to view the data, or log into their account for the server to view the data and other analysis. In another example, the device can emit a sound such as a beep or a voice recitation of any detected moisture via a speaker included in the device.

Furthermore, in different embodiments, the structural inspection device 210 can include provisions for broadcasting its location, for example via a location system. In some embodiments, the structural inspection device 210 may include its own GPS device and broadcast its latitude and longitude coordinates. In other embodiments, the location of a controller device, such as client computing device, may be paired with the range of structural inspection device 210. The location system can employ any type of positioning technology, such as but not limited to indoor positioning systems (IPS) that use radio frequency signals (RF), light-based or optical (i.e., both visible and infrared light) electromagnetic signals, sound signals (audible and ultrasonic), magnetic fields, Wireless Local Area Network (WLAN), Bluetooth, ZigBee, RFID, Ultrawideband (UWB), and/or passive/naturally occurring signals. The location system and sensors can work in conjunction with onboard communication system 240 to transmit data regarding location and/or sensor conditions to a remote server and/or the local client computing device.

As noted earlier in FIG. 1, the structural inspection device 210 is substantially enclosed or contained in a housing 220 that secures the plurality of components configured to communicate and monitor various external conditions. While in some embodiments the housing 220 of structural inspection device 210 includes a continuous waterproof or water-resistant casing, in other embodiments, the housing 220 can also include access points or openings to permit various functions or features. For example, in some embodiments, there may be connecting regions or openings for a translation mechanism, a gripping mechanism, and an input connector 242. For purposes of this application, a translation mechanism refers to a means by which the structural inspection device 210 is configured to travel or move. The drawings depict a plurality of wheels; however, in different embodiments, the device may include tracks, rollers, arms, hovercraft technology, coasters, or other translation mechanisms (propeller elements), also referred to as a motive system, working in conjunction with a motor 248 (e.g., electric motor, AC motor, brushed DC motor, brushless DC motor, geared DC motor, servo motor, stepper motor, etc.) to enable motion of the device as part of the propeller mechanism, in conjunction with a power supply (battery or other source). In some embodiments, the wheels are configured to allow the structural inspection device 210 to travel over bumps, electrical wiring, plumbing components, or supporting braces within the interior space between the two walls using for example, articulated wheeled assembly, use of 'sticky' feet (e.g., electroadhesive foot pads), etc.

In addition, particularly in cases where the structural inspection device 210 is to be deployed along a vertical surface, a gripping mechanism will be provided, such as one or more spring-loaded scissor components (e.g., see FIG. 1)

or other features that support the motion of the device in an upward and downward direction (e.g., adhesive elements, extendable arms, inflatable exterior that increases (inflates) in volume to move through wider spaces and decreases (deflates) in volume to move through smaller or more narrow spaces, etc.). Furthermore, the structural inspection device 210 can include a rechargeable battery 246 that may be recharged via a wireless or wired recharging apparatus, or via an inductive charging device (i.e., using the magnetic component “B” that is also present for use with the controller). Other embodiments of the structural inspection device 210 can have circuitry for harvesting RF power to charge the battery 246. In one embodiment, a charging cable or communication cable is connected to input connector 242 formed in the housing 220.

In some other embodiments, the structural inspection device 210 itself can include one or more buttons or switches that may be operable to perform one of more functions, such as pairing operations, powering on/off, and alert settings. Furthermore, in some embodiments, the structural inspection device 210 includes a clock that may add a time signal to any data transmitted from the structural inspection device 210. The assembly 200 may also be configured to alert user when a structural inspection device 210 leaves the range of the controller 250 and/or returns to the range of the controller 250. Different responses or alerts could be given at different ranges as the distance between the structural inspection device 210 and the controller 250 changes.

As noted above, in different embodiments, the assembly 200 can also include controller 250. It should be appreciated that the controller 250 depicted in FIG. 2 can be provided in a variety of implementations, including but not limited to a remote control, a passive magnetic attractive component, and/or a software application running on a computing device for the user. Thus, only some of the plurality of components shown in FIG. 2 for controller 250 may be present in the controller that is provided. In some embodiments, in the case of a software application (“app”) 262, the controller 250 is a mobile or other client computing device (controller computing system 260) with memory and processors that host the app 262. The app 262 can include a user interface, which will allow a user to access settings and operations related to sensors, navigation, and power for the structural inspection device 210.

Thus, in different embodiments, a client computing device such as a mobile device (e.g., cell phone) will be used to present a user interface for the structural inspection device (s). The user interface can provide (e.g., display and/or present) and/or receive information (e.g., data and/or images) to and/or from a user (e.g., operator) of the mobile device. For example, the user interface can include a screen (e.g., viewfinder) that can display images to the user of mobile device. As an example, user interface can display the image of the wall captured and sent to mobile device by a structural inspection device. In some embodiments, the user interface can display the image of the wall as an onboard sensor captures the image. That is, the user of mobile device can view the image (i.e., photos, livestream video or recorded video, etc.) as it is being captured by the sensor (e.g., the user can see what sensor sees).

In some embodiments, an end-user can interact with and adjust settings associated with the proposed assembly, for example via app 262. In some embodiments, the app 262 can offer a device registration and/or profile interface (“interface”) for implementing the assembly 200. In some embodiments, an application may be available that connects a user’s device (for example, via a Wi-Fi or cellular connection) with an online service provider or manager. For example, app 262 may connect to a remote server (“server”) via networks 270 to access or download updates for the app 262, create a user account, customize the user’s preferences or settings, generate a record showing previous assessment sessions stored as monitoring history and to maintain a profile or listing of registered structural inspection devices associated with the user account.

In different embodiments, a user can use the interface provided by application to change their user settings that may be stored in the cloud, and automatically update the corresponding settings and information. The application can offer a user interface that may be accessed via any user computing device configured for connection to a network. In different embodiments, the application can be configured to offer content via native controls presented via an interface. Throughout this application, an “interface” may be understood to refer to a mechanism for communicating content through a client application to an application user. In some examples, interfaces may include pop-up windows that may be presented to a user via native application user interfaces (UIs), controls, actuatable interfaces, interactive buttons or other objects that may be shown to a user through native application UIs, as well as mechanisms that are native to a particular application for presenting associated content with those native controls. In addition, the terms “actuation” or “actuation event” refers to an event (or specific sequence of events) associated with a particular input or use of an application via an interface, which can trigger a change in the display of the application. This can include selections or other user interactions with the application, such as a selection of an option offered via a native control, or a ‘click’, toggle, voice command, or other input actions (such as a mouse left-button or right-button click, a touchscreen tap, a selection of data, or other input types). Furthermore, a “native control” refers to a mechanism for communicating content through a client application to an application user. For example, native controls may include actuatable or selectable options or “buttons” that may be presented to a user via native application UIs, touch-screen access points, menus items, or other objects that may be shown to a user through native application UIs, segments of a larger interface, as well as mechanisms that are native to a particular application for presenting associated content with those native controls. The term “asset” refers to content that may be presented in association with a native control in a native application. As some non-limiting examples, an asset may include text in an actuatable pop-up window, audio associated with the interactive click of a button or other native application object, video associated with a teaching user interface, or other such information presentation.

In embodiments in which the controller 250 is configured as a hardware component (rather than a software app running on a client device), the controller 250 can also include a battery 274, a communication module 272 for transmitting signals to and receiving signals from the structural inspection device 210, a handheld housing component 276 that is sized and dimensioned for a human hand to hold and interact with, and in some embodiments, a magnetic component “A” which serves as the opposite magnetic pole or attractive force for engaging with the magnetic component “A” of the structural inspection device 210. This manipulation process will be shown in greater detail below.

Although the embodiments depicted in the drawings depict a wall crawler equipped to move along vertical surfaces, it should be appreciated that the structural inspection device can also be equipped to move along horizontal and irregular surfaces. For example, the structural inspection device can be deployed in an underground space and remain there indefinitely, performing regular or semi-regular inspections of the moisture content in the space. In another example, the structural inspection device can be deployed in the rafters or roofing area of the building, or some other elevated surface that is not accessible from the ground, such as, areas near hard to reach wall(s) or window(s), and remain there long-term. In another example, the structural inspection device(s) can be deployed throughout a structure during construction and periodically perform inspections of moisture content.

In another embodiment, structural inspection device(s) may be permanently or semi-permanently positioned within a structure and remotely operated to inspect the structure. For instance, structural inspection device(s) may be positioned within an attic. Onboard computing system of structural inspection device(s) may then be programmed to periodic perform inspections of structure. Such inspections may occur in accordance with a schedule at regular intervals through programming of a calendar or timer. Such inspections may occur on an ad hoc basis, such as in response to an event, e.g., a weather or sound event. For example, rain or hail on a roof could be sensed by sound or by a remote weather trigger from a weather radio frequency or by the Internet. In both instances, one or more onboard sensors may collect instantaneous, periodic, or continuous data collection depending on the event trigger (e.g., a rodent may trigger video and heavy rain may trigger two photos an hour apart). A sensor response may vary depending on other environmental variables, such as the temperature, barometric pressure, and humidity at the time of the event trigger. In one example, temperature change of an area and ambient temperature change are two variables that may cause the initiation of active observation of a leak such that the remedial focus may be on repair rather than replacement.

In one embodiment, structural inspection device(s) may be affixed to a structure. For instance, structural inspection device(s) may be suspended from a structure. Propeller elements attached to structural inspection device(s) 104 may be utilized to navigate structural inspection device(s) in a regular pattern through the structure. In another embodiment, structural inspection device(s) may be freestanding within a structure. Structural inspection device(s) may utilize ground propelling elements, such as wheels, coasters, or treads, to navigate through the structure.

Thus, the assembly is not to be understood to be limited to a wall inspection as it may encompass inspection of any portion of a structure (e.g., building, vehicles, and the like) susceptible to inspection by the systems and techniques described herein. For ease of description purposes, reference is herein made regarding to inspection of a wall and its interior space; however, the assembly should not be understood to be limited to these examples.

Figure 3:
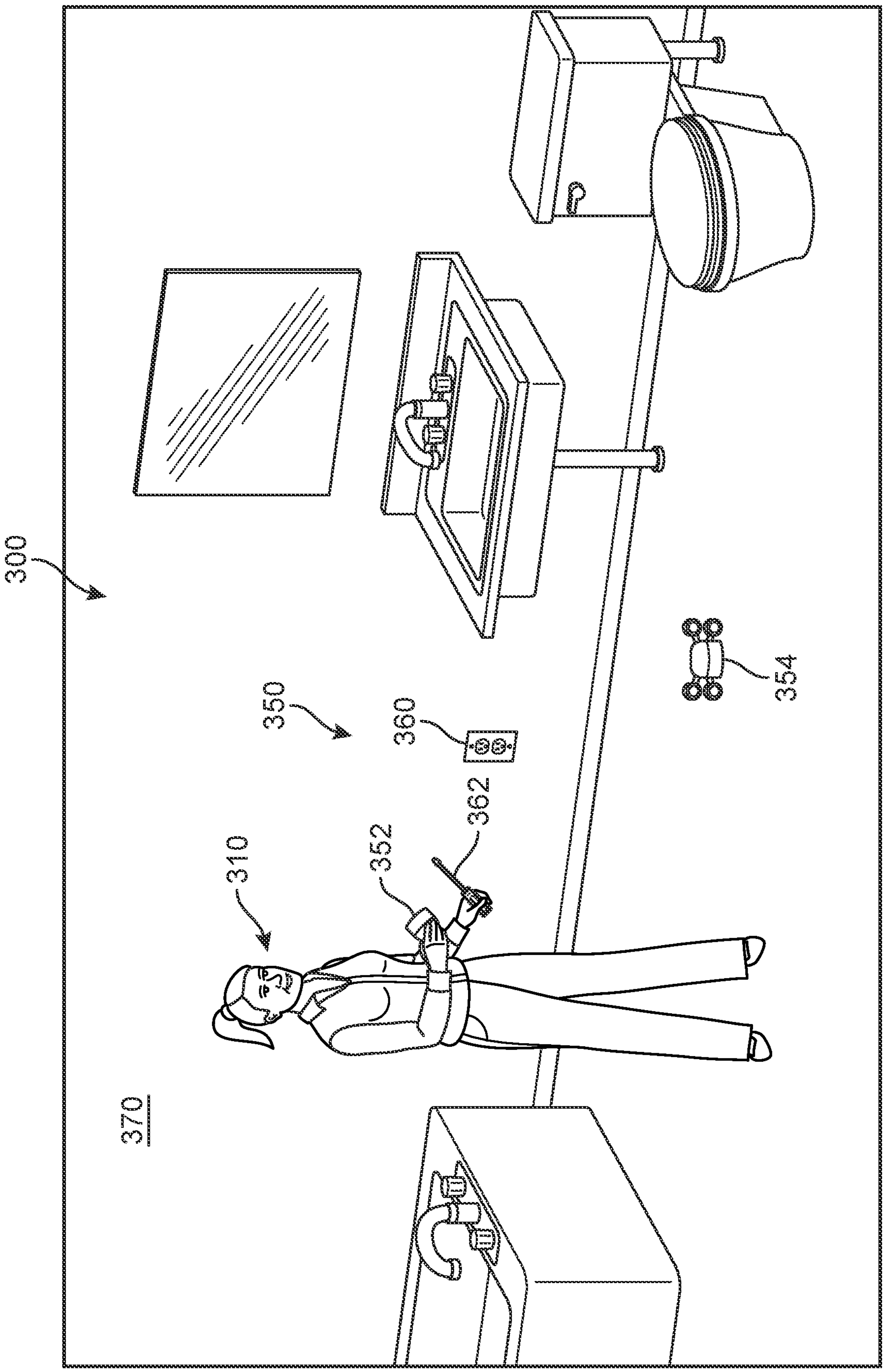
FIGS. 3 and 4 depict a user removing a cover for a wall outlet in preparation of deploying the structural inspection assembly, according to an embodiment.
Figure 4:
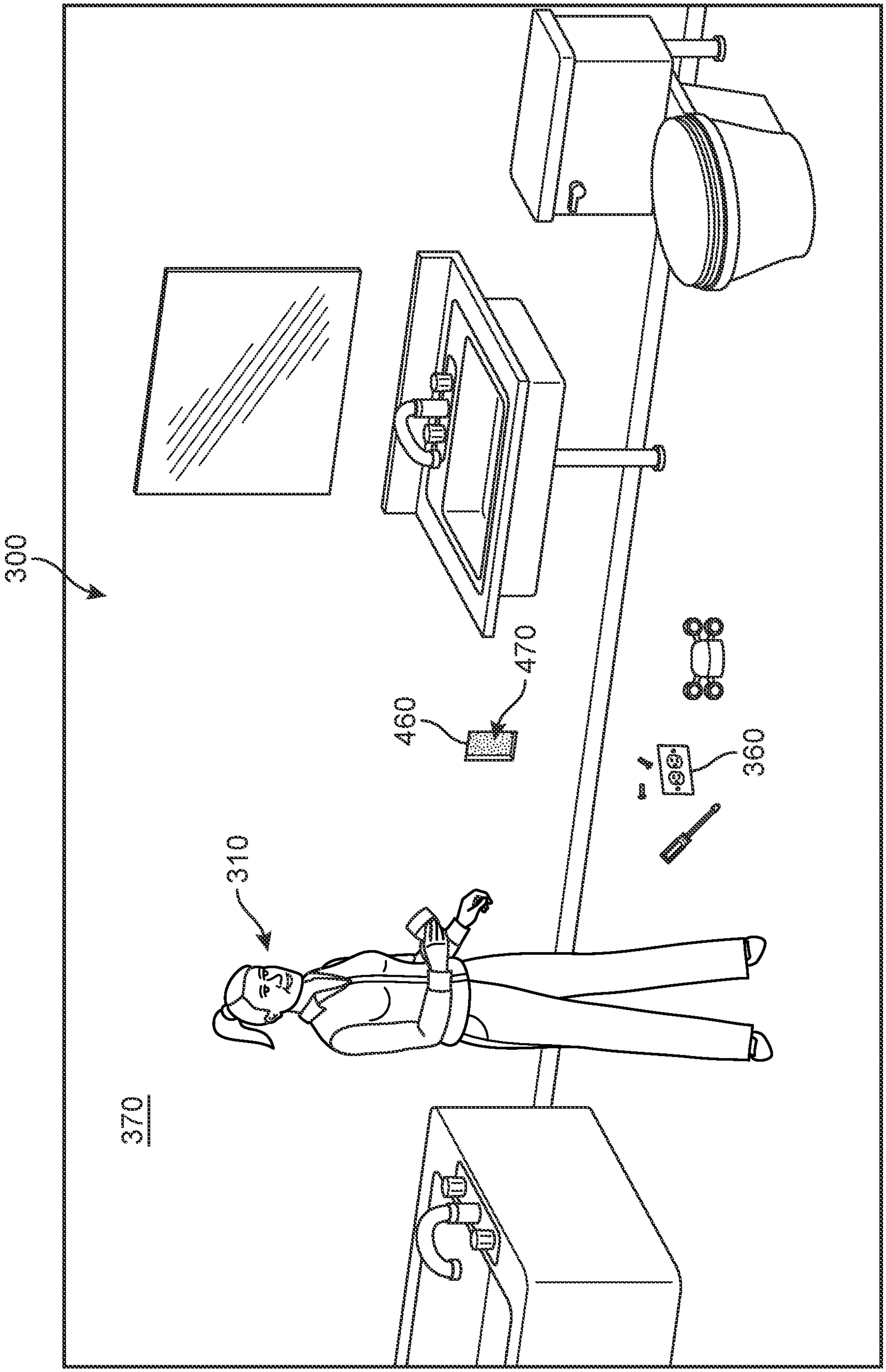

Referring now to FIGS. 3-7D, a sequence of drawings illustrates an example of some advantages and uses of an embodiment of a structural inspection assembly ("assembly") 350 for detection of moisture, pests, debris, and other potential structural irregularities. In FIG. 3, a first user 310 is standing in a bathroom space 300 that includes fixtures such as a bathtub, a sink, and a toilet. Each of these three fixtures are interconnected by a series of pipes comprising the local plumbing system. In FIG. 3, the first user 310 is preparing to initiate a moisture detection session with a controller 352 and a structural inspection device 354. In this case, the first user 310 is employing a screwdriver 362 (or other tool) to remove an exterior casing 360 for an electrical outlet formed on a first wall 370 for bathroom space 300. FIG. 4 shows the casing 360 has been removed, revealing a wall opening 460 formed in the first wall 370 that leads to or is in fluid communication with an interior space 470.

Figure 5:
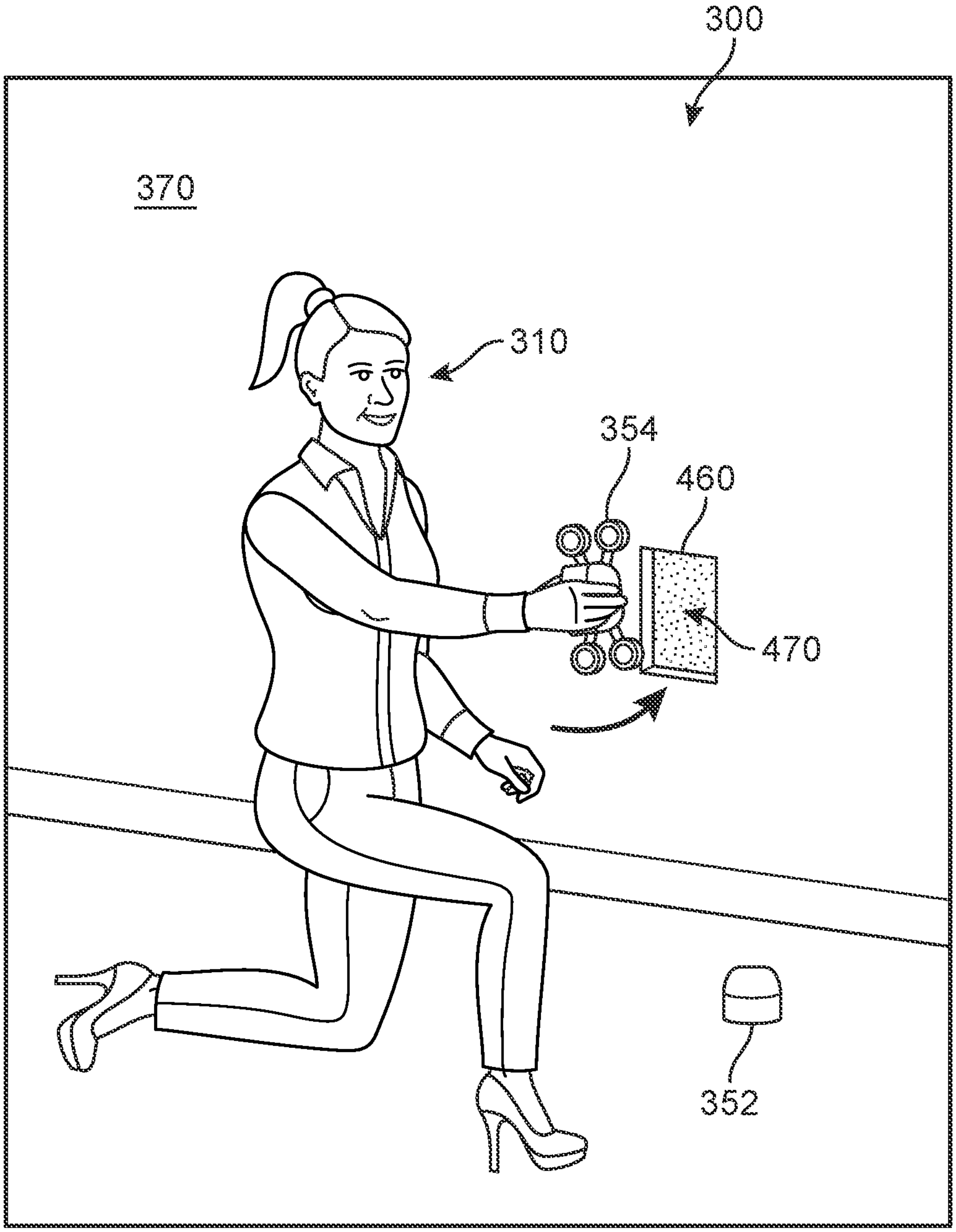
FIGS. 5 and 6 depict the user deploying the structural inspection device through the opening for the outlet, according to an embodiment.
Figure 6:
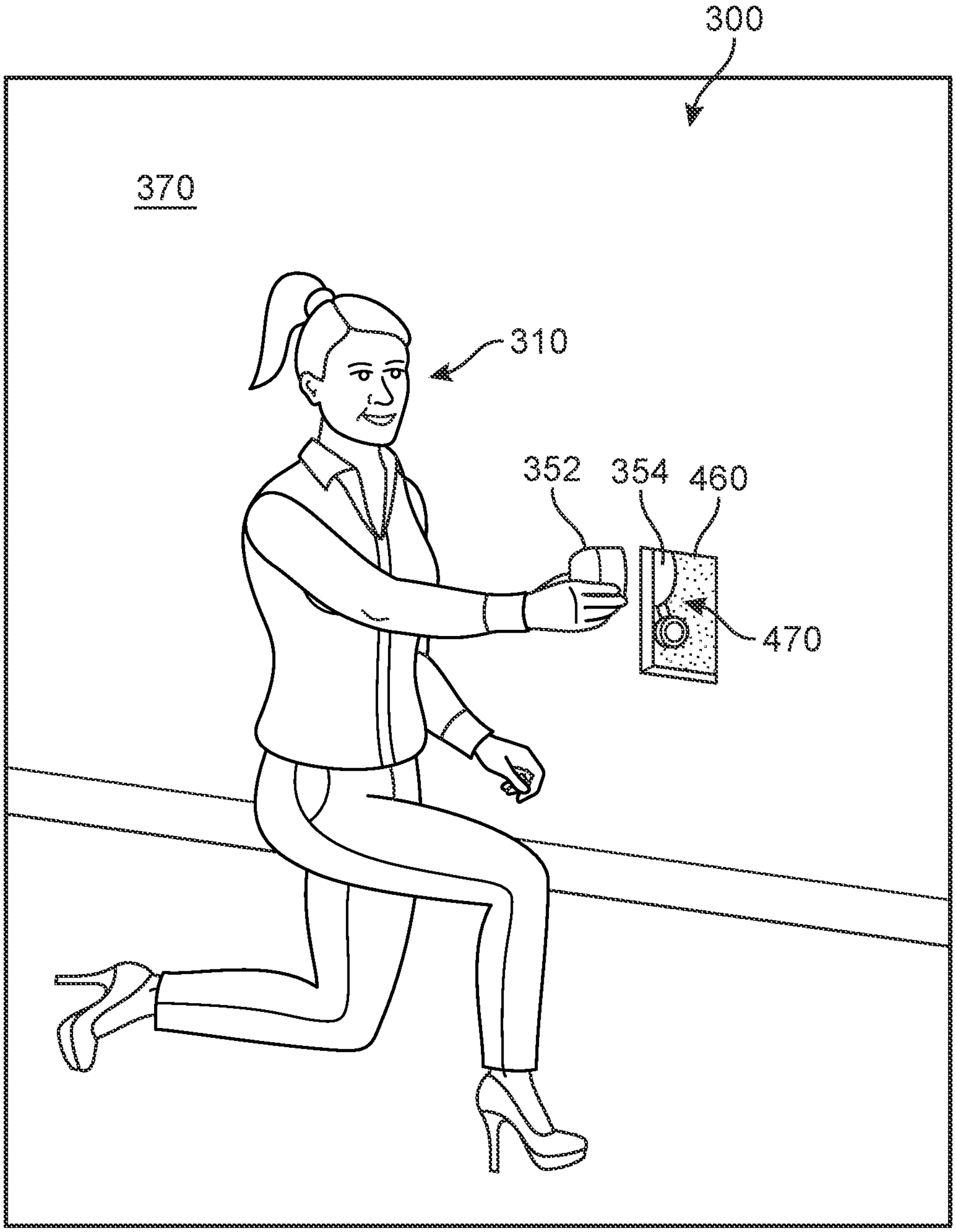
Figure 7B:
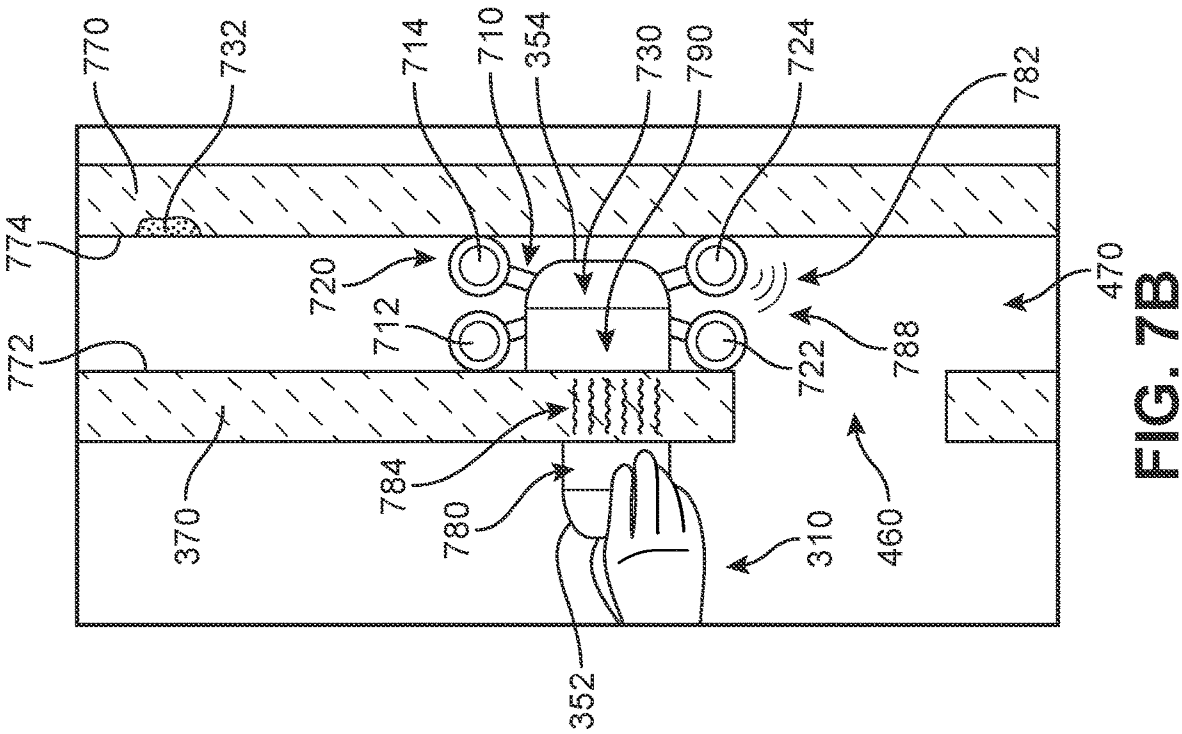
FIGS. 7A-7D is a sequence illustrating an example operation of the structural inspection assembly using magnet-based control, according to an embodiment.
Figure 7A:
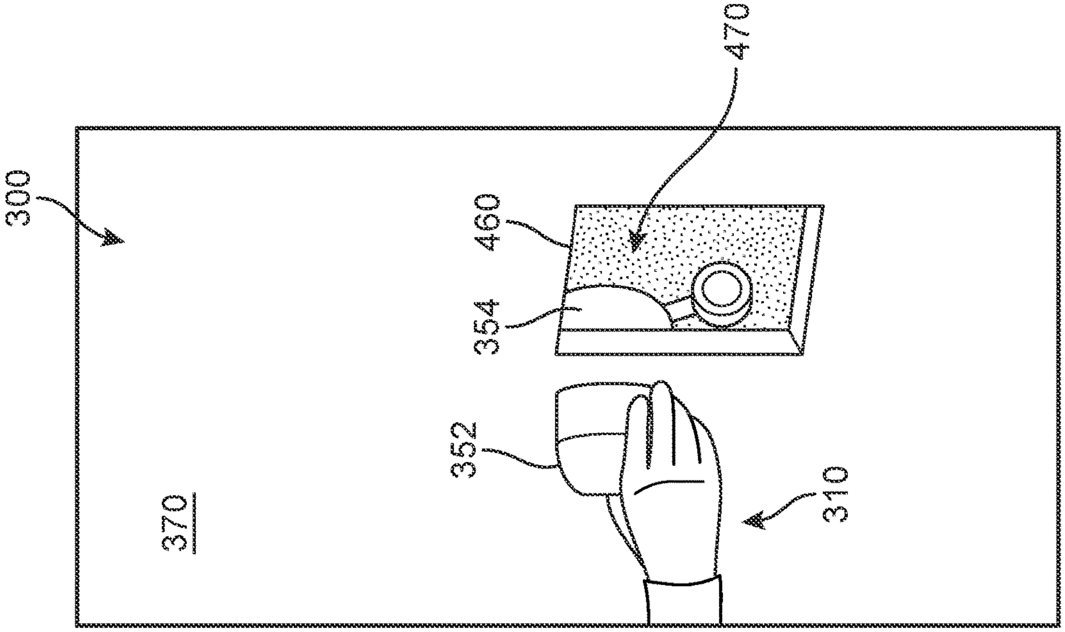

As shown in FIG. 5, in order to deploy the structural inspection device 354, first user 310 carries the structural inspection device 354 to the wall opening 460, and—in FIG. 6—inserts the structural inspection device 354 into the interior space 470. Referring now to the sequence of FIGS. 7A-7D, an embodiment of a process of controller navigation and moisture detection is shown. In FIG. 7A, the assembly 300 is shown as it is deployed in a magnified isometric side view. For purposes of clarity, the same arrangement of FIG. 7A is shown in a side cross-sectional view in FIG. 7B. In FIG. 7B, the interior space 470 can be seen to refer to a narrow channel or space extending between a first interior surface 772 of the first wall 370 and a second interior surface 774 of an opposing second wall 770. In other words, the interior space 470 is substantially enclosed by structural fixtures and features that generally preclude access by humans without first breaking some portion of the wall(s). The interior space 470 can be substantially empty in some embodiments, or include components such as electrical wiring and/or plumbing hardware, etc. In addition, while a vertical length of the interior space 470 (top to bottom) is shown as having a uniform width, in other embodiments, the width may vary, as well as the thickness of the surrounding walls.

As shown in FIG. 7B, propeller mechanism 788 comprises a first scissor hinge 710 with a pair of wheels (a first wheel 712 and a second wheel 714), and a second scissor hinge 720 with a pair of wheels (a third wheel 722 and a fourth wheel 724), each hinge disposed toward opposing ends of the structural inspection device 354. Each hinge is pushed or squeezed together (bringing the two wheels in each pair closer together) as the device is inserted into the interior space 470. The squeezing occurs in response to contact with the first interior surface 772 and second interior surface 774. In this case, the first wheel 712 and the third wheel 722 each press against the first interior surface 772, while the second wheel 714 and the fourth wheel 724 each press against the second interior surface 774. The hinge mechanism is pre-tensioned to bias the two scissor arms into an open or extended/expanded configuration, resisting retraction/closure, and so remains secured in place when not being propelled up or down. As the device rolls into a space where the two opposing surfaces are farther apart (wider), the hinge extends distally outward to maintain its grip and position. As the device rolls into a space where the two opposing surfaces are closer together (narrower), the hinge retracts proximally inward to permit the device to fit in the gap while maintaining its grip and position. Thus, the hinges enable the device to travel in a vertical direction through spaces of different dimensions. In other embodiments, other types of propeller mechanisms may be used.

In addition, for purposes of this example, controller 352 comprising a passive magnetic attractive force is being employed by the first user 310. Thus, a first magnetic component 780 is disposed in controller 352 that is configured to attract a second magnetic component 790 in the structural inspection device 354, represented schematically as magnetic force 784. Motion of one of the two can cause motion in the other; thus, in this type of arrangement, a motor is not required. In FIG. 7B, sensors 730 housed in the structural inspection device 354 are activated or enabled and begin to monitor the surrounding area for moisture content or other structural irregularities (e.g., water damaged portion 732). In some embodiments, the structural inspection device 354 can transmit/receive signals 782 to a client computing device or server over a network as described above. At this time, the sensors 730 have not yet detected the water damaged portion 732.

Figure 7C:
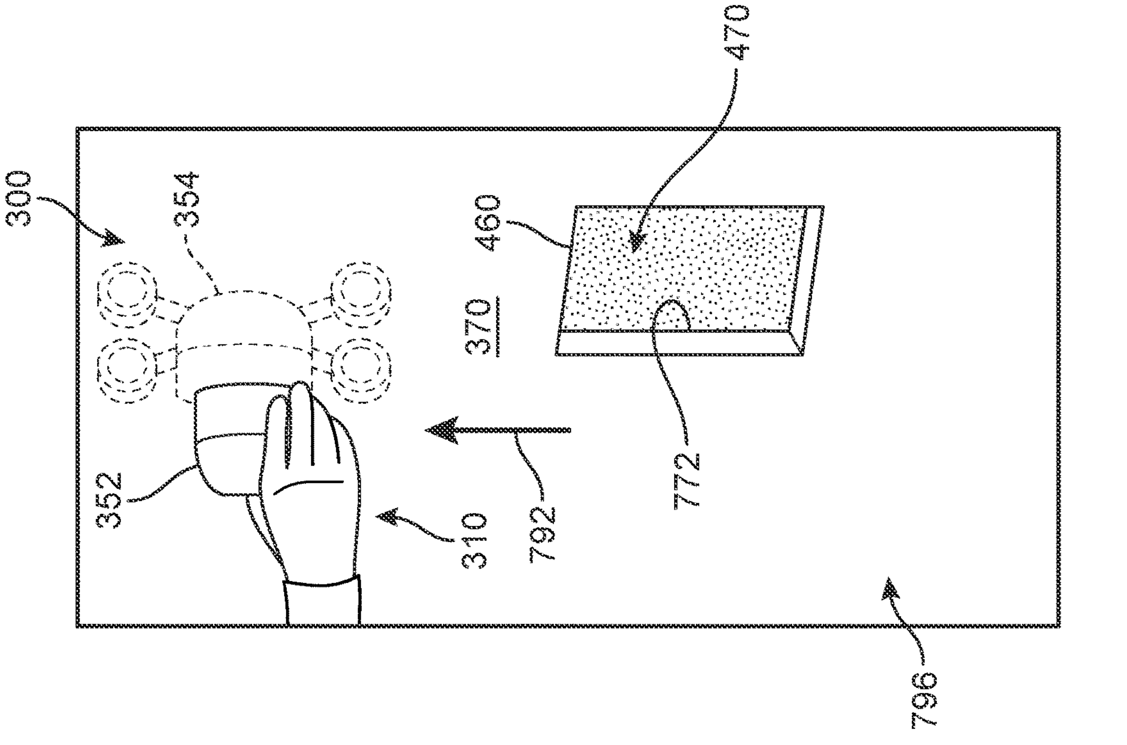
Figure 7D:
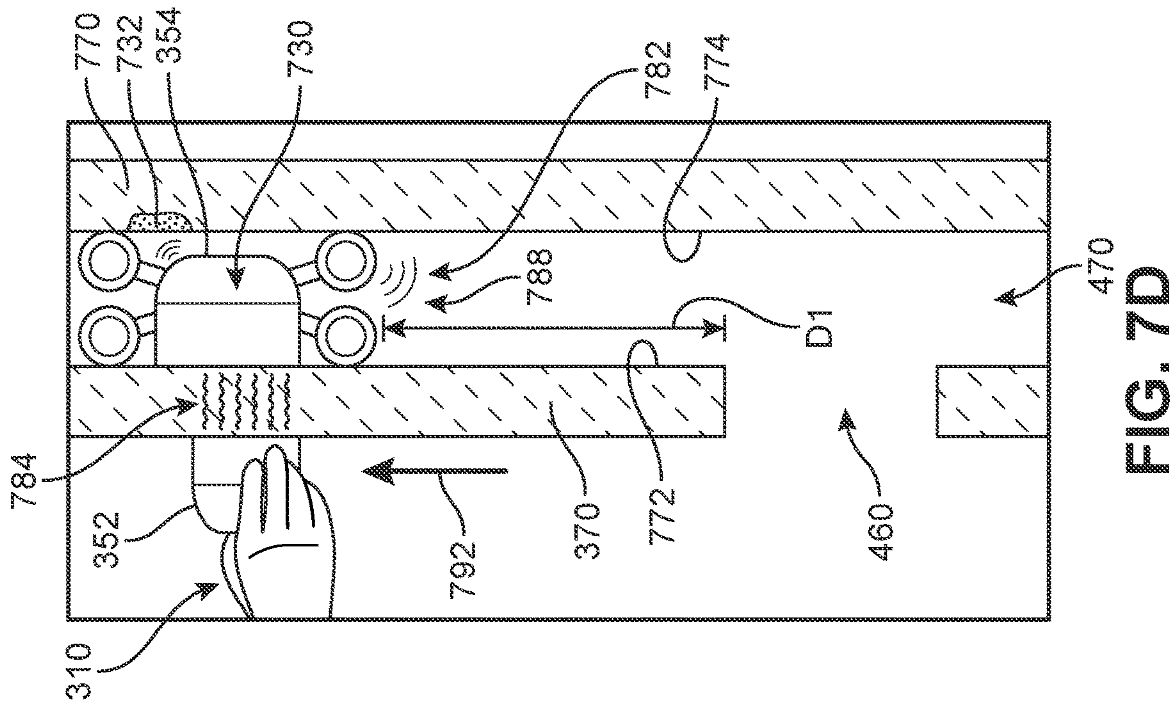

In FIG. 7C, the first user 310 is shown having moved their hand—which grasps the controller 352—in a generally upward direction 792 along an outer surface 796 of the first wall 370. In response, the structural inspection device 354 (shown in dotted line) moves/translates in a corresponding path on the opposite side of the first wall 370 (first interior surface 772) along interior space 470. The same action is shown in a cross-sectional view in FIG. 7D. The structural inspection device 354 has rolled along the two interior surfaces as the magnetic force 784 continues to exert its attraction between the two components. Having moved a first distance D1, the sensors 730 are now in range of the water damaged portion 732. The sensor data is acquired, and an onboard computing device or remote server receives and processes this data, determining the moisture level has exceeded a threshold or baseline that automatically triggers a notification or alert to the user. In some embodiments, the detection of a first region of moisture can cause the device to activate additional or more sensitive sensors that had been previously dormant or in a power-saving mode in order to ensure capture of the most accurate and/or precise readings.

Although a handheld controller is shown in the drawings, it should be understood that in other embodiments the structural inspection device can instead be paired via an app to a nearby computing device and is configured to transmit data to and receive data from the paired computing device while its inspection occurs substantially autonomously. The data can be transmitted as an electronic signal via device components such as radio frequency identification devices (RFID), radio transmitters and/or transceivers capable of transmitting and/or receiving including but not limited to one or more of the following types of signals and/or protocols: cellular network signals, Wi-Fi network signals, Bluetooth® signals, short or long range radio signals, RFID signals, infrared signals, sonic and ultrasonic signals, global positioning system (GPS) signals and other radio signals, optical and laser signals, and signals across any known spectrum of wavelengths and/or frequency.

Figure 8:
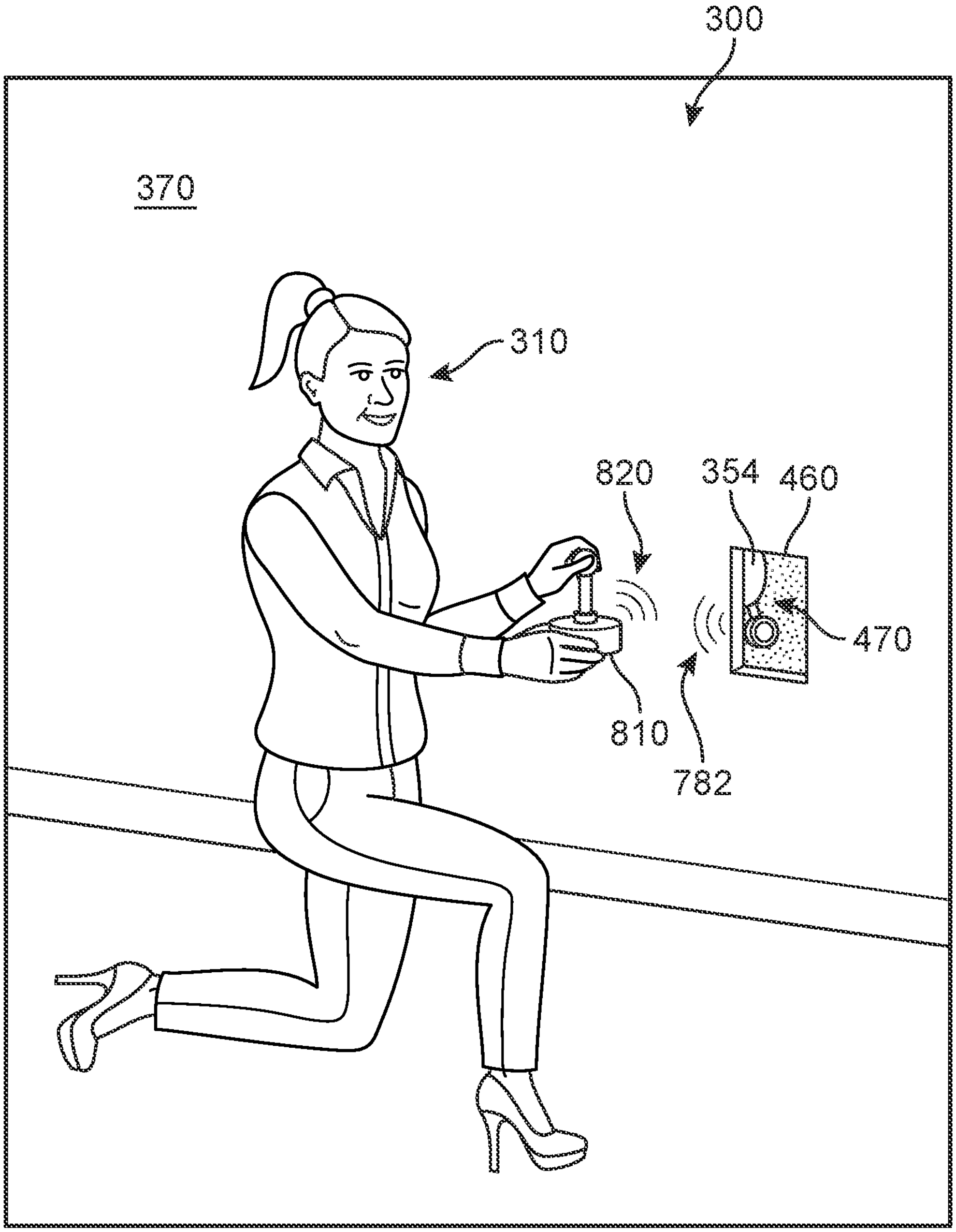
FIG. 8 is an illustration of an alternate joystick-type controller for a structural inspection device, according to an embodiment.
Figure 9:
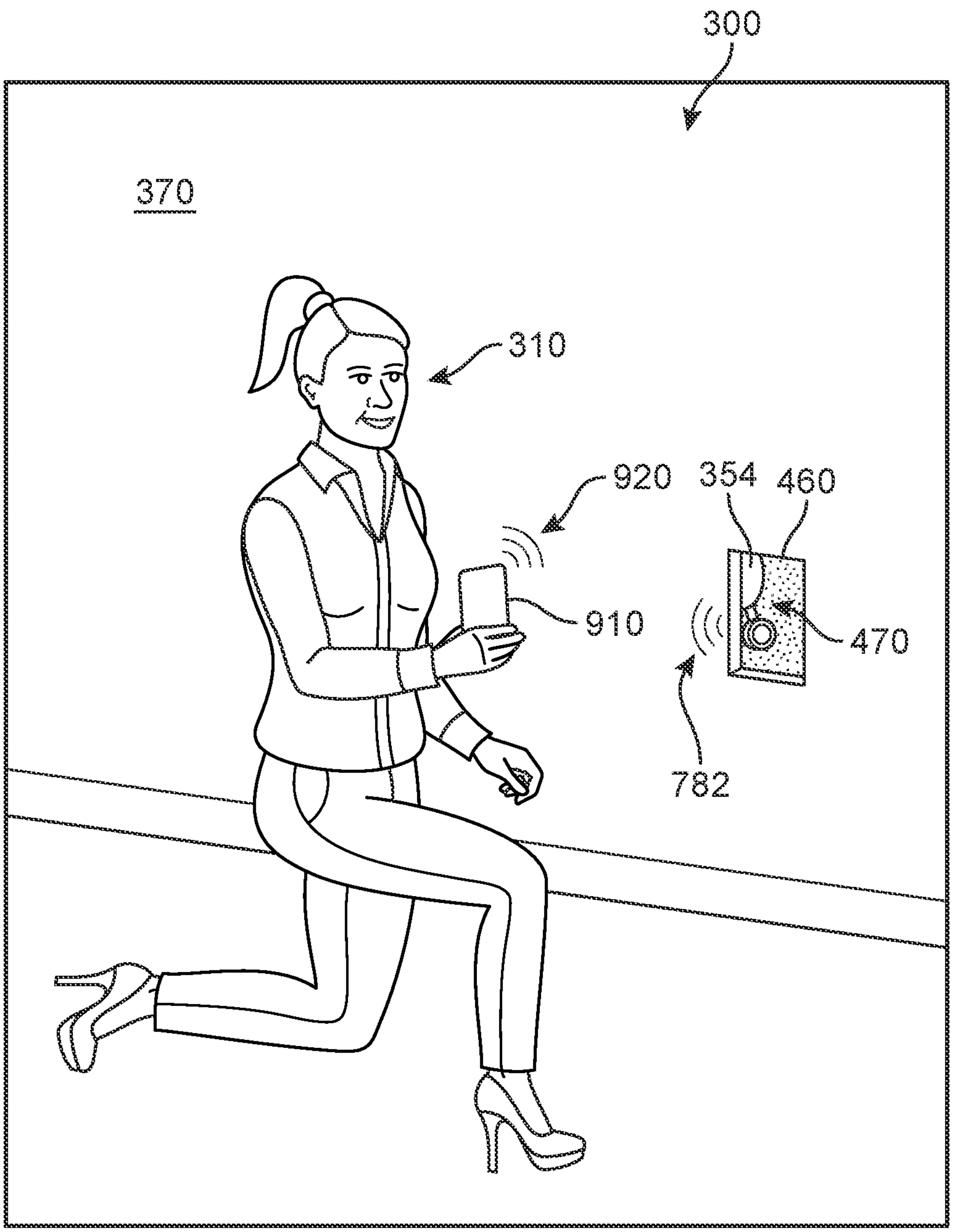
FIG. 9 is an illustration of an alternate software application-based controller for a structural inspection device, according to an embodiment.

For purposes of illustration, two alternate embodiments are shown in FIGS. 8 and 9. In FIG. 8, the first user 310 is shown employing a joystick 810 to send/receive signals 820 to/from structural inspection device 354. In this case, the onboard communication system is configured to accept the signals generated by the joystick 810. An onboard motor responds and propels the structural inspection device 354 according to the navigation commands provided by the joystick 810.

Figure 10:
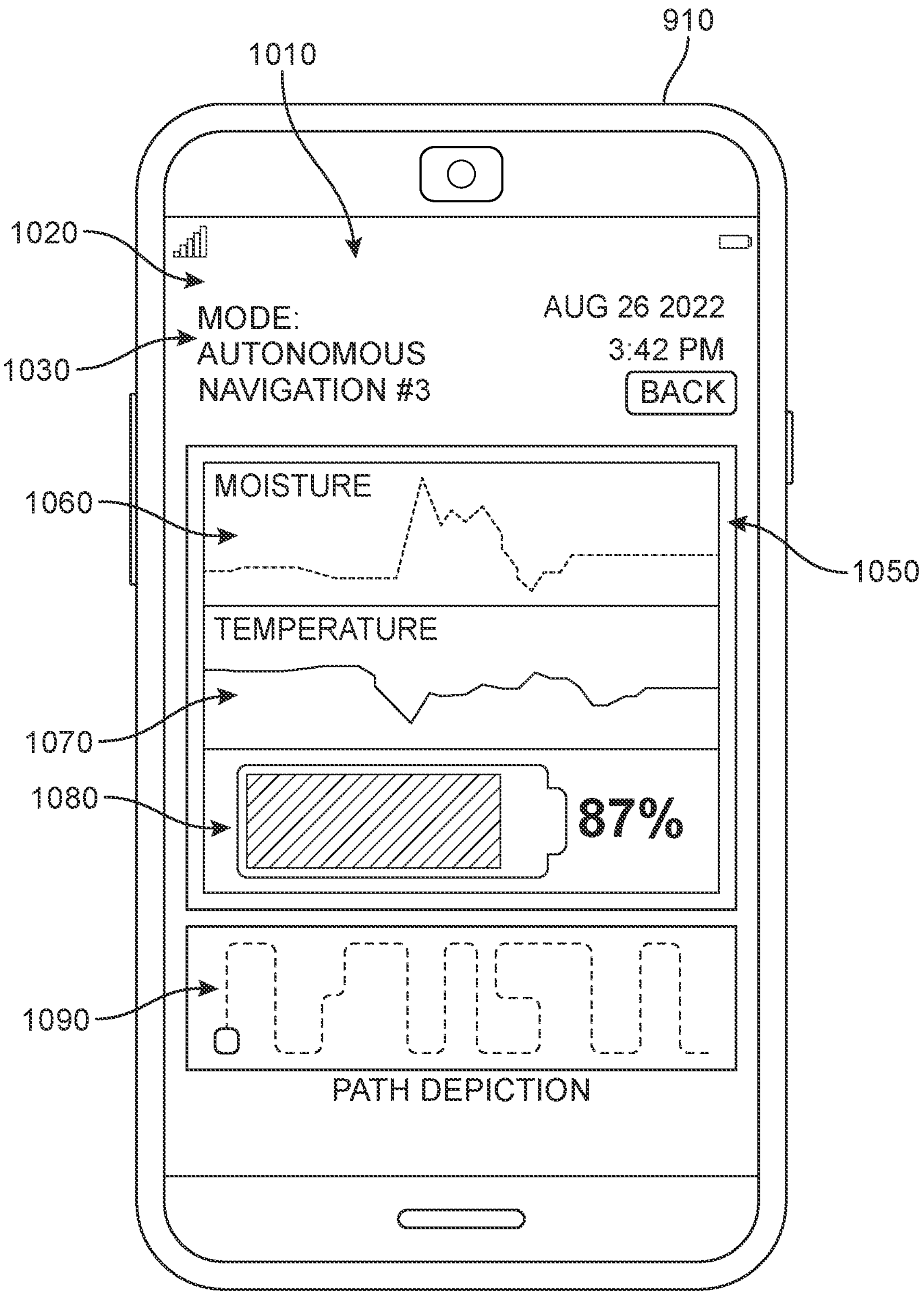
FIG. 10 is a depiction of an app for monitoring data collected by the structural inspection device and controlling the structural assessment device, according to an embodiment.

In another example, illustrated in FIG. 9, the first user 310 has downloaded a control app on a computing device (mobile phone) 910, which allows the mobile phone 910 to send/receive signals 920 to/from structural inspection device 354. In some embodiments, the control app includes a user interface that presents navigational control options. In FIG. 10, an example of an app 1020 presented on display 1010 of the mobile phone 910 is shown. In this case, the user has opted to engage an autonomous navigation mode 1030, such that the structural inspection device can travel with little to no navigational inputs from the user. In addition, the app 1020 presents a data panel or dashboard 1050 for review by the user. In this example, the dashboard 1050 includes a graphical representation of moisture content 1060, temperature 1070, and battery level 1080 for the structural inspection device. In addition, in some embodiments, a path depiction 1090 can be displayed that schematically illustrates the route the structural inspection device is traveling as it performs its inspection. In different embodiments, the app 1020 is configured to receive data from the sensors of structural inspection device and provide information to the user regarding the location and conditions associated with the structural inspection device. In some embodiments, additional messaging may be presented ("ALERT: moisture content above your maximum threshold in this area") can provide further information to the user. Other embodiments can include actuatable or other interactive options for the user to adjust settings, transmit instructions or commands, and/or view a more detailed report, as well as pinpoint the location of various sites that have been flagged for follow up by the device.

Figure 11:
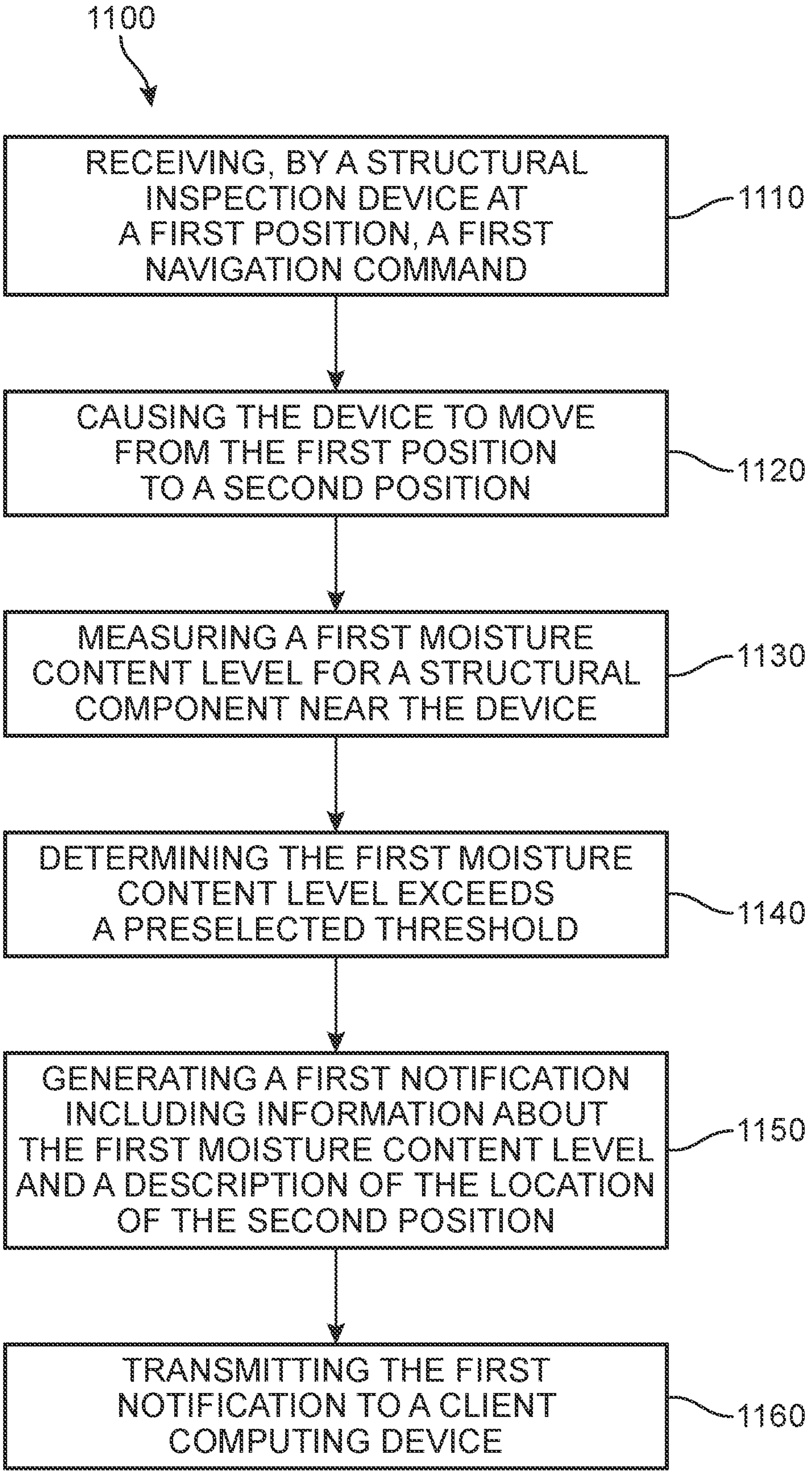
FIG. 11 is a flow chart showing the process by which a structural inspection assembly can detect damage to a structure, according to an embodiment.

FIG. 11 is a flow chart illustrating an embodiment of a method 1100 of detecting damage to a structure. The method 1100 includes a first step 1110 of receiving, by an onboard computing system of a structural inspection device located at a first position, a first navigation command, and a second step 1120 of causing a propelling mechanism of the structural inspection device to move the structural inspection device from the first position to a different, second position in response to the first navigation command. A third step 1130 includes measuring, while at the second position and via a first sensor of the structural inspection device, a first moisture content level for a structural component within range of the first sensor, and a fourth step 1140 of determining, at the onboard computing system, the first moisture content level exceeds a preselected threshold. The method 1100 also includes a fifth step 1150 of generating, via the onboard computing system, a first notification including information about the first moisture content level and a description of the location of the second position, and a sixth step 1160 of transmitting over a network and via a communications module of the structural inspection device, the first notification to a client computing device.

In other embodiments, the method may include additional steps or aspects. In one embodiment, the method the first navigation command is generated by a software application running on a local client computing device (e.g., via the app as described above), and in another example, the first navigation command is generated by an autonomous navigation engine or route determination engine of the onboard computing device. In some embodiments, the method 1100 also includes a step of automatically activating a second sensor that had previously been dormant in response to the first moisture content level exceeding the preselected threshold; for example, a second sensor may drain more power or otherwise be associated with a greater cost to operate, and so would only be enabled or used after data collected via a more cost-efficient 'gateway' sensor is used to determine a triggering event or condition has occurred. In different embodiments, the structural inspection device is sized and dimensioned to fit through a standard 1-Gang electrical outlet opening in a wall, traditionally used to install two plugs. For purposes of this application, a standard "1-Gang" electrical outlet opening or "cutout" in a wall is a rectangular aperture with dimensions ranging between approximately 1.5-3 inches by approximately 3-4.5 inches (e.g., 1.94" wide×3.06" high). However, in some other embodiments, the device can be larger, and sized and dimensioned to fit a 2-Gang electrical outlet opening, which typically ranges between approximately 2.5-5 inches by approximately 4-5.5 inches (e.g., 4.56" wide×4.5" tall), or even 3-Gang electrical box outlet openings (e.g., $5\frac{13}{16}$-Inch Length; $3\frac{5}{8}$-Inch Width).

In some embodiments, the method 1100 also includes steps of detecting, while at the second position and via a second sensor of the structural inspection device, a first structural irregularity within range of the second sensor, and then determining, at the onboard computing system, the first structural irregularity has a high likelihood of representing a pest, wherein the first notification further includes information about the detection of the pest. Thus, structural irregularity can be understood to refer broadly to areas in which presence undesirable objects (creatures), debris, or damage is determined as highly likely. In one embodiment, the structural inspection device moves from the first position to the second position by traveling in a vertical direction along an interior space between two walls, for example by employing a vertical crawler mechanism.

As described herein, some of the proposed embodiments can be understood to include a structural inspection assembly. The assembly includes a first device including a first magnetic component, and a first sensor configured to assess moisture content, as well as a second device including a second magnetic component with a magnetic field strong enough to exert a magnetic pulling force on and maintain a grip of the first magnetic component through at least a 1% inch thickness of drywall. In other embodiments, the magnetic field is strong enough to maintain a magnetic grip through up to two inches of drywall. The magnetic grip may also be maintained across other materials of different thicknesses, depending for example on the porosity of the material. As a general matter, the magnetic component will have a diameter and/or thickness that increases as the thickness of the structure being inspected increases. For example, if examining a wood wall with a thickness of $\frac{1}{16}$" (0.0625"), for a magnet thickness of $\frac{3}{16}$" (0.1875"), the magnet should have a diameter of at least 0.5". Similarly, for a wood wall with a thickness of $\frac{1}{8}$" (0.125"), if a magnet thickness of $\frac{1}{4}$" is selected for use in the device, it should also have at least a $\frac{5}{8}$" diameter.

In some embodiments, the first device is sized and dimensioned to fit through a cutout opening for a standard electrical outlet. In one example, the second device is sized and dimensioned to be held in a human hand. In different embodiments, the first sensor employs one or more of electrical tomography, gamma-rays, and X-rays to assess moisture content. In another embodiment, the first sensor employs a dielectric and/or microwave meter to assess moisture content. In still another embodiment, the first sensor employs a laser scanner to assess moisture saturation and movement in building materials. In some embodiments, the first sensor employs Ground-Penetrating Radar (GPR) to perform moisture detection. In different embodiments, the first device further includes an onboard computing system configured to process data collected by the first sensor and determine whether a moisture content for a portion of a structure exceeds a preselected threshold. As another example, the first device further includes a propeller system including a first pair of wheels mounted on a first scissor hinge extending from a first end of the first device. In some embodiments, the first device is protected by a water-resistant housing or case.

As a general matter, the proposed embodiments are directed to devices, systems, and methods of using a robotic (mobile) sensor unit to survey and/or inspect a property. The sensor(s) collect data and an onboard computing system or remote server receives the data and determines whether there is a higher-than-normal moisture content level, or other types of damage, such as a pattern of wear for at least one material used in a construction of the structure. In some embodiments, the data can be used to generate a real-time view of the structure for display on a user interface. in some embodiments, the sensor(s) are a multispectral sensor. The device can move within the structure while capturing the data, electronically transmit the data to a computer server, whereby the remote computer server electronically receives the data. The receiving component includes data analysis engines and ML models that analyze the captured data (e.g., onboard or in the computer server) to determine a condition of the structure and/or an identification of the material(s). In one example, the system can electronically transmit the condition of the structure to an operator of the assembly.

It is appreciated that methods in accordance with the present disclosure can include any combination of the aspects and features described herein. That is, methods and systems in accordance with the present disclosure are not limited to the combinations of aspects and features specifically described herein, but also include any combination of the aspects and features provided.

The processes and methods of the embodiments described in this detailed description and shown in the figures can be implemented using any kind of computing system having one or more central processing units (CPUs) and/or graphics processing units (GPUs). The processes and methods of the embodiments could also be implemented using special purpose circuitry such as an application specific integrated circuit (ASIC). The processes and methods of the embodiments may also be implemented on computing systems including read only memory (ROM) and/or random access memory (RAM), which may be connected to one or more processing units. Examples of computing systems and devices include, but are not limited to: servers, cellular phones, smart phones, tablet computers, notebook computers, e-book readers, laptop or desktop computers, all-in-one computers, as well as various kinds of digital media players.

The processes and methods of the embodiments can be stored as instructions and/or data on non-transitory computer-readable media. The non-transitory computer readable medium may include any suitable computer readable medium, such as a memory, such as RAM, ROM, flash memory, or any other type of memory known in the art. In some embodiments, the non-transitory computer readable medium may include, for example, an electronic storage device, a magnetic storage device, an optical storage device, an electromagnetic storage device, a semiconductor storage device, or any suitable combination of such devices. More specific examples of the non-transitory computer readable medium may include a portable computer diskette, a floppy disk, a hard disk, magnetic disks or tapes, a read-only memory (ROM), a random access memory (RAM), a static random access memory (SRAM), a portable compact disc read-only memory (CD-ROM), an erasable programmable read-only memory (EPROM or Flash memory), electrically erasable programmable read-only memories (EEPROM), a digital versatile disk (DVD and DVD-ROM), a memory stick, other kinds of solid state drives, and any suitable combination of these exemplary media. A non-transitory computer readable medium, as used herein, is not to be construed as being transitory signals, such as radio waves or other freely propagating electromagnetic waves, electromagnetic waves propagating through a waveguide or other transmission media (e.g., light pulses passing through a fiber-optic cable), or electrical signals transmitted through a wire.

Instructions stored on the non-transitory computer readable medium for carrying out operations of the present invention may be instruction-set-architecture (ISA) instructions, assembler instructions, machine instructions, machine dependent instructions, microcode, firmware instructions, configuration data for integrated circuitry, state-setting data, or source code or object code written in any of one or more programming languages, including an object oriented programming language such as Smalltalk, C++, or suitable language, and procedural programming languages, such as the "C" programming language or similar programming languages.

Aspects of the present disclosure are described in association with figures illustrating flowcharts and/or block diagrams of methods, apparatus (systems), and computing products. It will be understood that each block of the flowcharts and/or block diagrams can be implemented by computer readable instructions. The flowcharts and block diagrams in the figures illustrate the architecture, functionality, and operation of possible implementations of various disclosed embodiments. Accordingly, each block in the flowchart or block diagrams may represent a module, segment, or portion of instructions. In some implementations, the functions set forth in the figures and claims may occur in an alternative order than listed and/or illustrated.

The embodiments may utilize any kind of network for communication between separate computing systems. A network can comprise any combination of local area networks (LANs) and/or wide area networks (WANs), using both wired and wireless communication systems. A network may use various known communications technologies and/or protocols. Communication technologies can include, but are not limited to: Ethernet, 802.11, worldwide interoperability for microwave access (WiMAX), mobile broadband (such as CDMA, and LTE), digital subscriber line (DSL), cable internet access, satellite broadband, wireless ISP, fiber optic internet, as well as other wired and wireless technologies. Networking protocols used on a network may include transmission control protocol/Internet protocol (TCP/IP), multiprotocol label switching (MPLS), User Datagram Protocol (UDP), hypertext transport protocol (HTTP), hypertext transport protocol secure (HTTPS) and file transfer protocol (FTP) as well as other protocols.

Data exchanged over a network may be represented using technologies and/or formats including hypertext markup language (HTML), extensible markup language (XML), Atom, JavaScript Object Notation (JSON), YAML, as well as other data exchange formats. In addition, information transferred over a network can be encrypted using conventional encryption technologies such as secure sockets layer (SSL), transport layer security (TLS), and Internet Protocol security (Ipsec).

The computing devices and systems described herein may include one or more processors, a memory, one or more storage devices, and one or more input/output (I/O) devices controllable via one or more I/O interfaces. The various components may be interconnected via at least one system bus, which may enable the transfer of data between the various modules and components of the system.

The processor(s) may be configured to process instructions for execution within the system. The processor(s) may include single-threaded processor(s), multi-threaded processor(s), or both. The processor(s) may be configured to process instructions stored in the memory or on the storage device(s). The processor(s) may include hardware-based processor(s) each including one or more cores. The processor(s) may include general purpose processor(s), special purpose processor(s), or both. The memory may store information within the system. In some implementations, the memory includes one or more computer-readable media. The memory may include any number of volatile memory units, any number of non-volatile memory units, or both volatile and non-volatile memory units. The memory may include read-only memory, random access memory, or both. In some examples, the memory may be employed as active or physical memory by one or more executing software modules.

The storage device(s) may be configured to provide (e.g., persistent) mass storage for the system. In some implementations, the storage device(s) may include one or more computer-readable media. For example, the storage device (s) may include a floppy disk device, a hard disk device, an optical disk device, or a tape device. The storage device(s) may include read-only memory, random access memory, or both. The storage device(s) may include one or more of an internal hard drive, an external hard drive, or a removable drive.

One or both of the memory or the storage device(s) may include one or more computer-readable storage media (CRSM). The CRSM may include one or more of an electronic storage medium, a magnetic storage medium, an optical storage medium, a magneto-optical storage medium, a quantum storage medium, a mechanical computer storage medium, and so forth. The CRSM may provide storage of computer-readable instructions describing data structures, processes, applications, programs, other modules, or other data for the operation of the system. In some implementations, the CRSM may include a data store that provides storage of computer-readable instructions or other information in a non-transitory format. The CRSM may be incorporated into the system or may be external with respect to the system. The CRSM may include read-only memory, random access memory, or both. One or more CRSM suitable for tangibly embodying computer program instructions and data may include any type of non-volatile memory, including but not limited to: semiconductor memory devices, such as EPROM, EEPROM, and flash memory devices; magnetic disks such as internal hard disks and removable disks; magneto-optical disks; and CD-ROM and DVD-ROM disks. In some examples, the processor(s) and the memory may be supplemented by, or incorporated into, one or more application-specific integrated circuits (ASICs).

The system may include one or more I/O devices. The I/O device(s) may include one or more input devices such as a keyboard, a mouse, a pen, a game controller, a touch input device, an audio input device (e.g., a microphone), a gestural input device, a haptic input device, an image or video capture device (e.g., a camera), or other devices. In some examples, the I/O device(s) may also include one or more output devices such as a display, LED(s), an audio output device (e.g., a speaker), a printer, a haptic output device, and so forth. The I/O device(s) may be physically incorporated in one or more computing devices of the system, or may be external with respect to one or more computing devices of the system.

The system may include one or more I/O interfaces to enable components or modules of the system to control, interface with, or otherwise communicate with the I/O device(s). The I/O interface(s) may enable information to be transferred in or out of the system, or between components of the system, through serial communication, parallel communication, or other types of communication. For example, the I/O interface(s) may comply with a version of the RS-232 standard for serial ports, or with a version of the IEEE 1284 standard for parallel ports. As another example, the I/O interface(s) may be configured to provide a connection over Universal Serial Bus (USB) or Ethernet. In some examples, the I/O interface(s) may be configured to provide a serial connection that is compliant with a version of the IEEE 1394 standard. The I/O interface(s) may also include one or more network interfaces that enable communications between computing devices in the system, or between the system and other network-connected computing systems. The network interface(s) may include one or more network interface controllers (NICs) or other types of transceiver devices configured to send and receive communications over one or more networks, such as the network(s), using any network protocol.

Computing devices of the system may communicate with one another, or with other computing devices, using one or more networks. Such networks may include public networks such as the internet, private networks such as an institutional or personal intranet, or any combination of private and public networks. The networks may include any type of wired or wireless network, including but not limited to local area networks (LANs), wide area networks (WANs), wireless WANs (WWANs), wireless LANs (WLANs), mobile communications networks (e.g., 3G, 4G, Edge, etc.), and so forth. In some implementations, the communications between computing devices may be encrypted or otherwise secured. For example, communications may employ one or more public or private cryptographic keys, ciphers, digital certificates, or other credentials supported by a security protocol, such as any version of the Secure Sockets Layer (SSL) or the Transport Layer Security (TLS) protocol.

The system may include any number of computing devices of any type. The computing device(s) may include, but are not limited to: a personal computer, a smartphone, a tablet computer, a wearable computer, an implanted computer, a mobile gaming device, an electronic book reader, an automotive computer, a desktop computer, a laptop computer, a notebook computer, a game console, a home entertainment device, a network computer, a server computer, a mainframe computer, a distributed computing device (e.g., a cloud computing device), a microcomputer, a system on a chip (SoC), a system in a package (SiP), and so forth. Although examples herein may describe computing device(s) as physical device(s), implementations are not so limited. In some examples, a computing device may include one or more of a virtual computing environment, a hypervisor, an emulation, or a virtual machine executing on one or more physical computing devices. In some examples, two or more computing devices may include a cluster, cloud, farm, or other grouping of multiple devices that coordinate operations to provide load balancing, failover support, parallel processing capabilities, shared storage resources, shared networking capabilities, or other aspects.

Implementations and all of the functional operations described in this specification may be realized in digital electronic circuitry, or in computer software, firmware, or hardware, including the structures disclosed in this specification and their structural equivalents, or in combinations of one or more of them. Implementations may be realized as one or more computer program products, i.e., one or more modules of computer program instructions encoded on a computer readable medium for execution by, or to control the operation of, data processing apparatus. The computer readable medium may be a machine-readable storage device, a machine-readable storage substrate, a memory device, a composition of matter effecting a machine-readable propagated signal, or a combination of one or more of them. The term "computing system" encompasses all apparatus, devices, and machines for processing data, including by way of example a programmable processor, a computer, or multiple processors or computers. The apparatus may include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal that is generated to encode information for transmission to suitable receiver apparatus.

A computer program (also known as a program, software, software application, script, or code) may be written in any appropriate form of programming language, including compiled or interpreted languages, and it may be deployed in any appropriate form, including as a standalone program or as a module, component, subroutine, or other unit suitable for use in a computing environment. A computer program does not necessarily correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program may be deployed to be executed on one computer or on multiple computers that are located at one site or distributed across multiple sites and interconnected by a communication network.

The processes and logic flows described in this specification may be performed by one or more programmable processors executing one or more computer programs to perform functions by operating on input data and generating output. The processes and logic flows may also be performed by, and apparatus may also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any appropriate kind of digital computer. Generally, a processor may receive instructions and data from a read only memory or a random access memory or both. Elements of a computer can include a processor for performing instructions and one or more memory devices for storing instructions and data. Generally, a computer may also include, or be operatively coupled to receive data from or transfer data to, or both, one or more mass storage devices for storing data, e.g., magnetic, magneto optical disks, or optical disks. However, a computer need not have such devices. Moreover, a computer may be embedded in another device, e.g., a mobile telephone, a personal digital assistant (PDA), a mobile audio player, a GPS receiver, to name just a few. Computer readable media suitable for storing computer program instructions and data include all forms of nonvolatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory may be supplemented by, or incorporated in, special purpose logic circuitry.

To provide for interaction with a user, implementations may be realized on a computer having a display device, e.g., a CRT (cathode ray tube) or LCD (liquid crystal display)

monitor, for displaying information to the user and a keyboard and a pointing device, e.g., a mouse or a trackball, by which the user may provide input to the computer. Other kinds of devices may be used to provide for interaction with a user as well; for example, feedback provided to the user may be any appropriate form of sensory feedback, e.g., visual feedback, auditory feedback, or tactile feedback; and input from the user may be received in any appropriate form, including acoustic, speech, or tactile input.

Implementations may be realized in a computing system that includes a back end component, e.g., as a data server, or that includes a middleware component, e.g., an application server, or that includes a front end component, e.g., a client computer having a graphical user interface or a web browser through which a user may interact with an implementation, or any appropriate combination of one or more such back end, middleware, or front end components. The components of the system may be interconnected by any appropriate form or medium of digital data communication, e.g., a communication network. Examples of communication networks include a local area network ("LAN") and a wide area network ("WAN"), e.g., the Internet. The computing system may include clients and servers. A client and server are generally remote from each other and typically interact through a communication network. The relationship of client and server arises by virtue of computer programs running on the respective computers and having a client-server relationship to each other.

While this specification contains many specifics, these should not be construed as limitations on the scope of the disclosure or of what may be claimed, but rather as descriptions of features specific to particular implementations. Certain features that are described in this specification in the context of separate implementations may also be implemented in combination in a single implementation. Conversely, various features that are described in the context of a single implementation may also be implemented in multiple implementations separately or in any suitable subcombination. Moreover, although features may be described above as acting in certain combinations and even initially claimed as such, one or more features from a claimed combination may in some examples be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems may generally be integrated together in a single software product or packaged into multiple software products.

While various embodiments of the invention have been described, the description is intended to be exemplary, rather than limiting, and it will be apparent to those of ordinary skill in the art that many more embodiments and implementations are possible that are within the scope of the invention. Accordingly, the invention is not to be restricted except in light of the attached claims and their equivalents. Also, various modifications and changes may be made within the scope of the attached claims.

We claim:

1. A method of detecting damage to a structure, the method comprising:

receiving, by an onboard computing system of a structural inspection device located at a first position within an interior space of a wall between opposing or adjacent sheets of drywall, a first navigation command;

causing, in response to receiving the first navigation command, a vertical crawler mechanism of the structural inspection device to move the structural inspection device up or down in a vertical direction along an interior-facing, vertical surface of the wall from the first position to a different, second position;

measuring, while at the second position and via a first sensor of the structural inspection device, a first moisture content level for a structural component within range of the first sensor;

determining, at the onboard computing system, the first moisture content level exceeds a preselected threshold;

generating, via the onboard computing system, a first notification including information about the first moisture content level and a description of the location of the second position; and transmitting, over a network and via a communications module of the structural inspection device, the first notification to a client computing device.

2. The method of claim 1, wherein the first navigation command is generated by a software application running on a local client computing device.

3. The method of claim 1, wherein the first navigation command is generated by an autonomous navigation engine of the onboard computing device.

4. The method of claim 1, further comprising automatically activating a second sensor that had previously been dormant in response to the first moisture content level exceeding the preselected threshold.

5. The method of claim 1, wherein the structural inspection device is sized and dimensioned to fit through a standard electrical outlet opening in a wall.

6. The method of claim 1, further comprising:

detecting, while at the second position and via a second sensor of the structural inspection device, a first structural irregularity within range of the second sensor; and determining, at the onboard computing system, the first structural irregularity represents a pest, wherein the first notification further includes information about the detection of the first structural irregularity and determination.

7. The method of claim 1, wherein the structural inspection device includes a spring-biased scissor hinge stabilization mechanism that exerts pressure against each of two opposing sheets of drywall.

8. A system for detecting damage to a structure, the system comprising a processor and machine-readable media including instructions which, when executed by the processor, cause the processor to:

receive, by an onboard computing system of a structural inspection device located at a first position within an interior space of a wall between opposing or adjacent sheets of drywall, a first navigation command;

cause, in response to receiving the first navigation command, a vertical crawler mechanism of the structural inspection device to move the structural inspection device up or down in a vertical direction along an interior-facing, vertical surface of the wall from the first position to a different, second position;

measure, while at the second position and via a first sensor of the structural inspection device, a first moisture content level for a structural component within range of the first sensor;

determine, at the onboard computing system, the first moisture content level exceeds a preselected threshold;

generate, via the onboard computing system, a first notification including information about the first moisture content level and a description of the location of the second position; and transmit, over a network and via a communications module of the structural inspection device, the first notification to a client computing device.

9. The system of claim 8, wherein the instructions further cause the processor to automatically activate a second sensor that had previously been dormant in response to the first moisture content level exceeding the preselected threshold.

10. The system of claim 8, wherein the structural inspection device is sized and dimensioned to fit through a standard electrical outlet opening in a wall.

11. The system of claim 8, wherein the structural inspection device includes a spring-biased scissor hinge stabilization mechanism that exerts pressure against each of two opposing sheets of drywall.

12. The system of claim 8, wherein the first navigation command is generated by a software application running on a local client computing device.

13. The system of claim 8, wherein the first navigation command is generated by an autonomous navigation engine of the onboard computing device.

14. The system of claim 8, wherein the instructions further cause the processor to:

detect, while at the second position and via a second sensor of the structural inspection device, a first structural irregularity within range of the second sensor; and determine, at the onboard computing system, the first structural irregularity represents a pest, wherein the first notification further includes information about the detection of the first structural irregularity and determination.

15. A system for detecting damage to a structure, the system comprising one or more computers and one or more storage devices storing instructions that are operable, when executed by the one or more computers, to cause the one or more computers to:

receive, by an onboard computing system of a structural inspection device located at a first position within an interior space of a wall between opposing or adjacent sheets of drywall, a first navigation command;

cause, in response to receiving the first navigation command, a vertical crawler mechanism of the structural inspection device to move the structural inspection device up or down in a vertical direction along an interior-facing, vertical surface of the wall from the first position to a different, second position;

measure, while at the second position and via a first sensor of the structural inspection device, a first moisture content level for a structural component within range of the first sensor;

determine, at the onboard computing system, the first moisture content level exceeds a preselected threshold;

generate, via the onboard computing system, a first notification including information about the first moisture content level and a description of the location of the second position; and transmit, over a network and via a communications module of the structural inspection device, the first notification to a client computing device.

16. The system of claim 15, wherein the first navigation command is generated by a software application running on a local client computing device.

17. The system of claim 15, wherein the first navigation command is generated by an autonomous navigation engine of the onboard computing device.

18. The system of claim 15, wherein the instructions further cause the one or more computers to automatically activate a second sensor that had previously been dormant in response to the first moisture content level exceeding the preselected threshold.

19. The system of claim 15, wherein the structural inspection device is sized and dimensioned to fit through a standard electrical outlet opening in a wall.

20. The system of claim 15, wherein the instructions further cause the one or more computers to:

detect, while at the second position and via a second sensor of the structural inspection device, a first structural irregularity within range of the second sensor; and determine, at the onboard computing system, the first structural irregularity represents a pest, wherein the first notification further includes information about the detection of the first structural irregularity and determination.

* * * * *